US012797620B2

(12) United States Patent
Goil et al.

(10) Patent No.: US 12,797,620 B2
(45) Date of Patent: Nov. 17, 2026

(54) METHOD AND SYSTEMS FOR USING CONDUCTIVE COMMUNICATION TO CONVEY INFORMATION BETWEEN AN IMPLANTABLE MEDICAL DEVICE AND AN EXTERNAL DEVICE

(71) Applicant: Pacesetter, Inc., Sylmar, CA (US)

(72) Inventors: Aditya Goil, Stevenson Ranch, CA (US); Gene A. Bornzin, Simi Valley, CA (US); Thanh Tieu, Sylmar, CA (US); Robert J. Williams, San Jose, CA (US); Alexander R. Bornzin, Los Angeles, CA (US)

(73) Assignee: Pacesetter, Inc., Sylmar (CA)

( * ) Notice: Subject to any disclaimer, the term of this patent is extended or adjusted under 35 U.S.C. 154(b) by 894 days.

(21) Appl. No.: 18/179,240

(22) Filed: Mar. 6, 2023

(65) Prior Publication Data

US 2023/0321447 A1 Oct. 12, 2023

Related U.S. Application Data

(60) Provisional application No. 63/328,779, filed on Apr. 8, 2022.

(51) Int. Cl.

*A61N 1/372* (2006.01)
*H04L 25/08* (2006.01)

(52) U.S. Cl.

CPC ........ *A61N 1/37223* (2013.01); *H04L 25/085* (2013.01)

(58) Field of Classification Search

CPC ............ A61N 1/37211; A61N 1/37217; A61N 1/37223; A61B 5/305; A61B 5/277; A61B 5/302

See application file for complete search history.

(56) References Cited

U.S. PATENT DOCUMENTS

| | | | | |
|---|---|---|---|---|
| 7,904,180 B2 * | 3/2011 | Juola | A61N 1/046 | 600/397 |
| 8,315,705 B2 * | 11/2012 | Keuninckx | H04B 5/26 | 607/57 |
| 9,522,280 B2 | 12/2016 | Fishler et al. | | |

(Continued)

OTHER PUBLICATIONS

Chi et al. "Dry-Ciontact and noncontact biopotential electrodes: Methodological Review" IEEE Reviews in Biomedical Engineering, vol. 3, 2010 (14 pages).

(Continued)

*Primary Examiner* — George R Evanisko

(74) *Attorney, Agent, or Firm* — Dean D. Small; Carroll, Hoette & Butscher, LLC

(57) ABSTRACT

A device comprises external electrodes configured to be held proximate to a patient's skin and to sense conductive communication signals transmitted by an implantable medical device (IMD) within the patient. A dielectric layer is provided on at least a first electrode of the external electrodes to space the first electrode apart from the patient's skin to form a non-contact capacitively coupled interface between the patient's skin and the first electrode. The capacitively coupled interface is sensitive to the conductive communication signals. A circuit is connected to the external electrodes and is configured to output a differential signal corresponding to the conductive communication signals.

20 Claims, 10 Drawing Sheets

(56) References Cited

U.S. PATENT DOCUMENTS

| | | | | |
|---|---|---|---|---|
| 10,299,700 | B2 * | 5/2019 | Forsell | A61N 1/37217 |
| 10,549,105 | B2 | 2/2020 | Klimovitch et al. | |
| 10,806,401 | B2 | 10/2020 | Volpe et al. | |
| 11,116,448 | B1 | 9/2021 | Trapero Martin et al. | |
| 11,357,414 | B2 | 6/2022 | Andersen | |
| 2020/0405168 | A1 | 12/2020 | Gabrin et al. | |
| 2021/0045660 | A1 | 2/2021 | Rader et al. | |
| 2021/0236832 | A1 | 8/2021 | Amsler et al. | |
| 2021/0308470 | A1 | 10/2021 | Fishler et al. | |
| 2021/0319894 | A1 | 10/2021 | Sobol et al. | |

OTHER PUBLICATIONS

Wannenburg et al. “Wireless Capatitive-Based ECG Sensing for Feature Extraction and Mobile Health Monitoring” IEEE Sensors Journal, vol. 18, No. 14, 2018 (10 pages).

Chi et al. “Wireless Non-contact Cardiac and Neural Monitoring” Conference: Proceedings of Wireless Health 2010 (9 pages).

* cited by examiner

METHOD AND SYSTEMS FOR USING CONDUCTIVE COMMUNICATION TO CONVEY INFORMATION BETWEEN AN IMPLANTABLE MEDICAL DEVICE AND AN EXTERNAL DEVICE

CROSS-REFERENCE TO RELATED APPLICATIONS

This application claims priority to U.S. Provisional Patent Application No. 63/328,779, filed 8 Apr. 2022, titled METHOD AND SYSTEMS FOR USING CONDUCTIVE COMMUNICATION TO CONVEY INFORMATION BETWEEN AN IMPLANTABLE MEDICAL DEVICE AND AN EXTERNAL DEVICE". The subject matter of the provisional application is expressly incorporated herein by reference in its entirety.

BACKGROUND

Embodiments of the present disclosure generally relate to methods and devices for conductive communication between an implantable medical device and an external device, with or without active participation of the patient.

An implantable medical device (IMD), such as a leadless pacemaker (LP), needs to communicate with a non-implanted device, or external device (ED), from time to time so that the non-implanted device can, e.g., program the implantable device, interrogate the implantable device, and/or obtain notifications and/or other types of diagnostic information from the implantable device. Typically, an LP is only capable of communicating with a non-implanted programmer that is operated by medical personnel, such as a physician or clinician. Accordingly, in many cases an LP can only communicate with a non-implanted device when the patient visits a medical office that owns or otherwise has access to a non-implanted programmer.

Communication between an LP and a non-implanted device may be facilitated by conductive communication via patient tissue. The use of conductive communication of information provides certain improvements over more conventional radio frequency (RF) and inductive communication techniques. For example, conductive communication techniques enable communication without requiring the non-implanted device to be held close to a patient or in a precise position relative to an implant site for an extended period of time. Conductive communication also enables power consumption to be reduced due to substantially lower current requirements and by eliminating peak power demands currently imposed by existing inductive and RF communication techniques. This can beneficially extend the life of an LP. Also, conductive communication techniques use elements generally already existing in an LP, such as the therapeutic electrodes that function as an input-output device, enabling elimination of a coil or an antenna that are conventionally used for inductive and RF communication and reducing complexity and component count significantly.

In order to perform conductive communication, at least two skin electrodes (that are part of or coupled to a non-implanted device) are attached directly to skin of a patient within which one or more IMDs and/or LPs is/are implanted, and the skin electrodes are used to transmit information to and/or receive information from the LP(s) via conduction through body tissue of the patient. One potential problem with using conductive communication is that the orientation of the LP(s) can cause fading that can adversely affect both programmer-to-implant (p2i) communication and implant-to-programmer (i2p) communication. More specifically, certain orientations of an LP may cause conductive communication to be intermittent or stop completely, which may occur when an electric potential field generated between programmer skin electrodes has too small a difference between the electrodes of the LP.

As discussed above, the patient is often required to travel to a medical facility to have the LP interrogated by a non-implanted device. This is time consuming for both the patient and the medical personnel, as well as costly to the patient in terms of increasing their medical bills. Additional problems arise when the patient attempts to use the technique away from a medical professional, such as at home (e.g., remote care). The patient needs to remove clothing in order to place the skin electrodes in contact with their skin with gel, tape, or other adhesive. Patient skin condition (e.g., wet, oily, dry, hairy) can vary, as can the high skin-electrode impedance (e.g., approximately 1 M Ohm) which can be a detrimental factor when using electrodes with a dc connection, resulting in reliability issues. Also, the skin electrodes have to be placed so that various ones of the skin electrodes and/or various skin locations do not accidentally connect with each other, creating possible short circuit paths, or experience the communication issues discussed previously. Further, the patient needs to understand how to attach and/or position the skin electrodes and/or be compliant with an often unskilled caregiver, such as a family member. Therefore, it would be beneficial if an LP can be interrogated from time to time without requiring that a patient visit a medical facility, and without requiring the patient or caregiver to position and attach the skin electrodes.

Accordingly, a need remains for methods and devices that improve the communication between a non-implanted device and one or more IMDs, such as an LP.

SUMMARY

In accordance with an embodiment, a device comprises external electrodes configured to be held proximate to a patient's skin and to sense conductive communication signals transmitted by an implantable medical device (IMD) within the patient. A dielectric layer is provided on at least a first electrode of the external electrodes to space the first electrode apart from the patient's skin to form a non-contact capacitively coupled interface between the patient's skin and the first electrode. The capacitively coupled interface is sensitive to the conductive communication signals. A circuit is connected to the external electrodes and is configured to output a differential signal corresponding to the conductive communication signals.

Optionally, the external electrodes further comprise a second electrode and a ground electrode, and the first and second electrodes are configured to sense the conductive communication signals while the ground electrode is configured to form at least one of a passive or driven grounding node to the patient's skin. At least two of the first, second and ground electrodes are spaced apart from the patient's skin by corresponding dielectric layers. The circuit further comprises a feedback circuit joined to the ground electrode to form the driven grounding node. The feedback circuit is configured to supply a feedback signal back into the patient to at least partially remove a common mode component within the conductive communication signals sensed by the first and second electrodes.

Optionally, the circuit includes a differential circuit configured to detect a potential difference, exhibited between the first electrode and a second electrode from the external electrodes, due to the conductive communication signals. The conductive communication signals can have a frequency of at least 100 kHz.

Optionally, the device further comprises a memory configured to store program instructions and a processor that, when executing the program instructions, is configured to process the differential signal to identify a communications message transmitted from the IMD within the conductive communication signals. The processor is further configured to process the differential signal by detecting a pulse train including the communications message, and to process the differential signal by detecting a first pulse having a first frequency followed by the pulse train having a second frequency.

Optionally, the non-contact capacitively coupled interface includes a thin layer of an insulating material, as the dielectric layer, to separate metal surfaces of the first and second electrodes from the patient's skin. The non-contact capacitively coupled interface is configured to pass the conductive communication signals with a frequency of at least 100 kHz and to block or at least partially attenuate signals below 100 Hz.

Optionally, a garment is configured to hold the external electrodes proximate to the patient's skin. The garment includes the dielectric layer to space the first electrode apart from the patient's skin to form the non-contact capacitively coupled interface between the patient's skin and the first electrode.

In accordance with embodiments herein, a computer implemented method comprises locating external electrodes proximate to a patient's skin and utilizing the external electrodes to sense conductive communication signals transmitted by an implantable medical device (IMD) within the patient. The method forms a non-contact capacitively coupled interface between the patient's skin and at least a first electrode from the external electrodes by providing a dielectric layer between the first electrode and the patient's skin to space the first electrode apart from the patient's skin. The capacitively coupled interface is sensitive to the conductive communication signals. The method utilizes a circuit, connected to the external electrodes, to output a differential signal corresponding to the conductive communication signals.

Optionally, the external electrodes further comprise a second electrode and a ground electrode. The method further comprises sensing the conductive communication signals with the first and second electrodes and forming at least one of a passive or driven grounding node to the patient's skin with the ground electrode. The method further comprises forming a non-contact capacitively coupled interface between the patient's skin and at least two of the first electrode, second electrode and ground electrode by spacing the external electrodes apart from the patient's skin by corresponding dielectric layers. The circuit is further configured to supply a feedback signal back into the patient to at least partially remove a common mode component within the conductive communication signals sensed by the first and second electrodes.

Optionally, the differential signal further corresponds to a potential difference, exhibited between the first electrode and a second electrode from the external electrodes, due to the conductive communication signals. Optionally, the method further comprises processing the differential signal to identify a communications message transmitted from the IMD within the conductive communication signals.

In accordance with embodiments herein, a computer implemented method comprises providing a device comprising: i) external electrodes configured to be held proximate to a patient's skin and to sense conductive communication signals transmitted by an implantable medical device (IMD) within the patient, ii) a dielectric layer provided on at least a first electrode from the external electrodes to space the first electrode apart from the patient's skin to form a non-contact capacitively coupled interface that is sensitive to the conductive communication signals between the patient's skin and the first electrode, and iii) a circuit connected to the external electrodes that is configured to output a differential signal corresponding to the conductive communication signals. Under control of one or more processors, wherein the one or more processors are configured with specific executable instructions, the method measures sensing vectors between the first electrode and a second electrode, between the first electrode and a third electrode, and between the second electrode and the third electrode. Two of the external electrodes are selected to be sense electrodes based on differential signals associated with each of the sensing vectors. One of the external electrodes is identified as a ground electrode and is located separate from the sense electrodes.

Optionally, the sense electrodes are selected based on the sensing vector with the largest differential signal. Optionally, the method further comprises supplying a feedback signal based on the conductive communication signals sensed by the sense electrodes to the ground electrode to at least partially remove a common mode component.

DETAILED DESCRIPTION

Figure 1A:
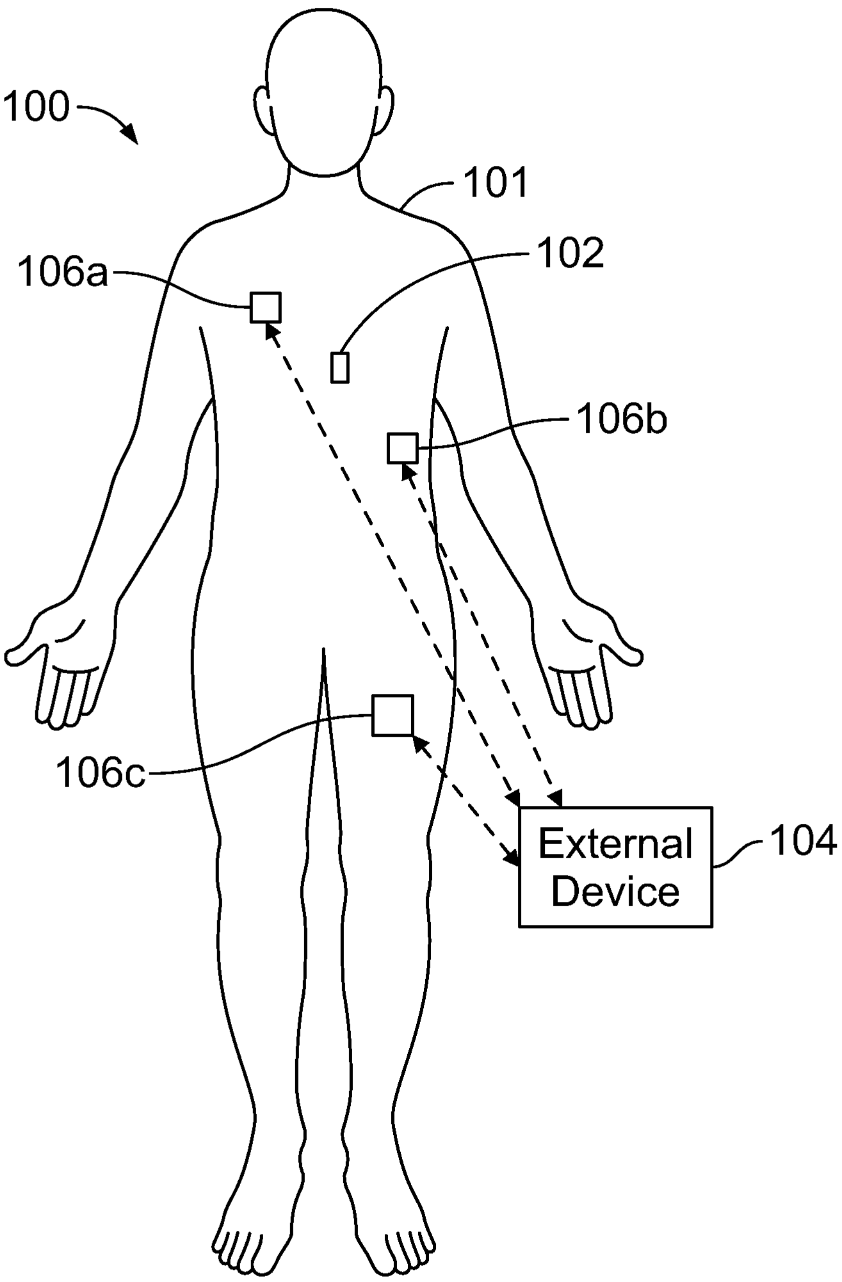
FIG. 1A illustrates a system that includes a plurality of external electrodes for communicating bi-directionally with an external device (ED) and an implantable medical device in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "sensing vector" shall refer to a path extending between two or more physical, actual external electrodes positioned outside of a patient's skin that operate as sensing sites. The sensing vector can be an indication of a size and/or quality of a differential signal and is based on conductive communication signals sensed by the external electrodes.

The term "non-contact", when used to describe a spacing between an external electrode and skin, shall mean that a surface of the external electrode is in physical contact with a first surface of a non-air dielectric layer, and that the skin is in physical contact with the opposite surface of the dielectric layer.

The term "therapeutic electrode" shall refer to the therapeutic electrode(s) located within, on, or within a few centimeters of a housing of an implantable medical device such as a leadless pacemaker. The therapeutic electrode(s) are used for pacing and sensing at the cardiac chamber, and for bidirectional communication, such as with conductive communication signals, with an external device located external of the patient.

The term "external electrode" shall refer to an electrode that is positioned external with respect to, and held/located proximate to, the skin surface of a patient's skin. The external electrode can be a capacitive electrode capable of sensing and transmitting, thus facilitating bi-directional communication via conductive communication signals.

The terms "external device", "ED", "remote monitor", and "external remote monitor" shall refer to any electronic device (or combination of devices) that can include circuitry, electronics, software, hardware, etc., that is not implanted within a patient's body and is external with respect to skin surface of the patient. The ED is configured to communicate with an implantable medical device, compare sensed signals, and configure components as needed. Non-limiting examples of EDs include a programmer, bed-side monitor, smart phone, tablet computer, laptop computer, desktop computer, server, personal advisory module (PAM), personal data assistant (PDA), and/or other devices capable of performing wired and wireless communication, and may include an application and/or circuitry capable of facilitating the methods and protocols discussed herein.

The term "common mode component" shall refer to a portion of a conductive communication signal that is attributed to a common mode signal, for example a 60 Hz signal, in the United States that can be present in a patient's body due to household/building electrical signals.

The terms "communications message" and "conductive communication message" shall refer to conductive communication that can be formatted in various manners. Communications message can include one or more of a leading trigger pulse, one or more time gap, data packets, a pulse train, different pulse durations, and frequency ranges. Information related to a device, such as an implantable medical device, an external device, and/or a patient can be included in the communications message.

The terms "dielectric", "dielectric barrier", and "dielectric layer" shall refer to a medium that has a dielectric constant. The medium can be a non-eddy current carrying medium. The medium can be a material that is positioned between, and in physical contact with, a surface (e.g., metallic surface) of the external electrode and the patient's skin. The dielectric can include any material that is not only air, such as one or more materials such as fabric (e.g., cotton, synthetics such as polyester, etc.) one or more polymers, a non-conductive coating such as parylene in a polymer, and the like. In some cases, the dielectric can have a dielectric constant approximately less than 15, although is not so limited.

The term "form factor" shall refer to an overall design and functionality of physical objects that include some or all of the components of the system described herein, such as including some, all, or a portion of the capacitive electrodes and, in some cases, the external device. Form factors include, but are not limited to, items such as a garment (e.g., clothing, shirt, pants, shorts, undergarments, etc.), blanket, pillow, and the like.

The terms "cardiac activity signal", "cardiac activity signals", "CA signal" and "CA signals" (collectively "CA signals") are used interchangeably throughout to refer to measured signals indicative of cardiac activity by a region or chamber of interest. For example, the CA signals may be indicative of impedance, electrical or mechanical activity by one or more chambers (e.g., left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes EGM signals. Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3, and/or S4 heart sounds. Impedance based CA signals refer to impedance measurements recorded along an impedance vector between two or more electrodes, where the impedance measurements are indicative of cardiac activity.

The terms "health care system" and "digital health care system" shall refer to a system that includes equipment for measuring health parameters, and communication pathways from the equipment to secondary devices. The secondary devices may be at the same location as the equipment, or remote from the equipment at a different location. The communication pathways may be wired, wireless, over the air, cellular, in the cloud, etc. In one example, the health care system provided may be one of the systems described in U.S. published application US20210020294A1, entitled "METHODS DEVICE AND SYSTEMS FOR HOLISTIC INTEGRATED HEALTHCARE PATIENT MANAGEMENT" filed Jul. 16, 2020, the entire contents of which are incorporated in full herein. Other patents that describe example monitoring systems include U.S. Pat. No. 6,572,557, entitled SYSTEM AND METHOD FOR MONITORING PROGRESSION OF CARDIAC DISEASE STATE USING PHYSIOLOGIC SENSORS, issued Jun. 2, 2003; U.S. Pat. No. 6,480,733 entitled METHOD FOR MONITORING HEART FAILURE filed Dec. 17, 1999, to Turcott; U.S. Pat. No. 7,272,443 entitled SYSTEM AND METHOD FOR PREDICTING A HEART CONDITION BASED ON IMPEDANCE VALUES USING AN IMPLANTABLE MEDICAL DEVICE, filed Dec. 14, 2004, to Min et al; U.S. Pat. No. 7,308,309 entitled DIAGNOSING CARDIAC HEALTH UTILIZING PARAMETER TREND ANALYSIS, filed Jan. 11, 2005, to Koh; and U.S. Pat. No. 6,645,153 entitled SYSTEM AND METHOD FOR EVALUATING RISK OF MORTALITY DUE TO CONGESTIVE HEART FAILURE USING PHYSIOLOGIC SENSORS, filed Feb. 7, 2002, to Kroll et. al., the entire contents of which are incorporated in full herein.

The term "IMD data" shall refer to any and all types of information and signals conveyed from an implantable medical device to a local or remote external device. Non-limiting examples of IMD data include cardiac activity signals (e.g., intracardiac electrogram or IEGM signals), impedance signals (e.g., cardiac, pulmonary or transthoracic impedances), accelerometer signatures (e.g., activity signals, posture/orientation signals, heart sounds), pulmonary arterial pressure (PAP) signals, MCS rpm levels, MCS flow rates, device alerts and the like.

The terms "obtains" and "obtaining", as used in connection with data, signals, information and the like, include at least one of i) accessing memory of an external device or remote server where the data, signals, information, etc., are stored, ii) receiving the data, signals, information, etc., over a wireless communications link between the IMD and a local external device, and/or iii) receiving the data, signals, information, etc., at a remote server over a network connection. The obtaining operation, when from the perspective of an IMD, may include sensing new signals in real time, and/or accessing memory to read stored data, signals, information, etc., from memory within the IMD. The obtaining operation, when from the perspective of a local external device, includes receiving the data, signals, information, etc., at a transceiver of the local external device where the data, signals, information, etc., are transmitted from an IMD and/or a remote server. The obtaining operation may be from the perspective of a remote server, such as when receiving the data, signals, information, etc., at a network interface from a local external device and/or directly from an IMD. The remote server may also obtain the data, signals, information, etc., from local memory and/or from other memory, such as within a cloud storage environment and/or from the memory of a workstation or clinician external programmer.

The term "POC" shall mean point-of-care. The term "point-of-care" and "POC", when used in connection with medical diagnostic testing, shall mean methods and devices configured to provide medical diagnostic testing at or near a time and place of patient care. The time and place of patient care may be at an individual's home, such as when providing "at home" point of care solutions. The time and place of patient care may be at a physician's office or other medical facility, wherein one or more medical diagnostic tests may be performed on-site at a time of or shortly after a patient visit and collection of a patient sample. The POC may implement the methods, devices and systems described in one or more of the following publications, all of which are expressly incorporated herein by reference in their entireties: U.S. Pat. No. 6,786,874, entitled "APPARATUS AND METHOD FOR THE COLLECTION OF INTERSTITIAL FLUIDS" issued Sep. 7, 2004; U.S. Pat. No. 9,494,578, entitled "SPATIAL ORIENTATION DETERMINATION IN PORTABLE CLINICAL ANALYSIS SYSTEMS" issued Nov. 15, 2016; and U.S. Pat. No. 9,872,641, entitled "METHODS, DEVICES AND SYSTEMS RELATED TO ANALYTE MONITORING" issued Jan. 23, 2018.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The term "real-time" refers to a time frame contemporaneous with normal or abnormal episode occurrences. For example, a real-time process or operation would occur during or immediately after (e.g., within minutes or seconds after) a cardiac event, a series of cardiac events, an arrhythmia episode, and the like. For example, the term "real-time" may refer to a time period substantially contemporaneous with an event of interest. The term "real-time", when used in connection with collecting and/or processing data utilizing an IMD, shall refer to processing operations performed substantially contemporaneous with a physiologic event of interest experienced by a patient.

The term "subcutaneous" shall mean below the skin, but not intravenous. For example, a subcutaneous electrode/lead does not include an electrode/lead located in a chamber of the heart, in a vein on the heart, or in the lateral or posterior branches of the coronary sinus.

The term "treatment notification" shall mean a communication and/or device command to be conveyed to one or more individuals and/or one or more other electronic devices, including but not limited to, network servers, workstations, laptop computers, tablet devices, smart phones, IMDs, external diagnostic test "EDT" equipment and the like. When a treatment notification is provided as a communication, the treatment notification may be represented in an audio, video, vibratory or other user perceivable medium. The communication may be presented in various formats, such as to display patient information, messages, user directions and the like. The communication is presented on one or more of the various types of electronic devices described herein and may be directed to a patient, a physician, various medical personnel, various patient record management personnel and the like.

System Overview

In accordance with new and unique aspects herein, methods and devices are described that establish bi-directional conductive communication between an implantable medical device and an external device. The conductive communication is accomplished using external electrodes that sense conductive communication signals transmitted by the implantable medical device. At least one of the external electrodes is spaced apart from the patient's skin with a dielectric layer.

The methods and devices can connect the available external electrodes into different configurations, and then evaluate the sensed conductive communication signals in the different configurations to identify the configuration with the strongest and/or best signal. One of the external electrodes can be passively grounded, while in other cases, the ground electrode can be actively grounded by driving a common mode rejection signal back into the patient's body through the active ground electrode. This can remove the common mode component of the signal and improve the quality of the conductive communication signals.

Additionally, an advantage is that the system can control the communication parameters, such as by controlling the size of external electrodes and distance of the active surface of the external electrode(s) from the patient's skin, resulting in repeatable and reliable communication when using a known or estimated dielectric. The conductive communication signals can be, at least, i) signals communicating with a device, ii) a signal that is being modified, such as by an external device, and iii) a common mode rejection signal.

FIG. 1A illustrates a system 100 in accordance with embodiments herein. The system 100 includes one implantable medical device (IMD) 102, such as a leadless pacemaker (LP) located in or proximate to a select chamber of the heart. In other embodiments, the IMD 102 can be located within the patient and outside the heart. Optionally, the system 100 can include two or more IMDs (e.g., two or more LPs). The IMD 102 can be referred to as an implanted or implantable subsystem. The implantable subsystem can include alternative and/or additional implantable devices, such as an ICD, as described below with reference to FIG. 1B.

The IMD 102 is configured to communicate bi-directionally with an external device (ED) 104 through a plurality of external electrodes 106*a*, 106*b*, 106*c*, such as to convey ED and/or IMD data, such as in real-time. The external electrodes 106 are capacitive electrodes. The ED 104 periodically and/or in response to a stimulus (e.g., request by user or system), establishes bi-directional communications with the IMD 102 to receive data that can be uploaded, wirelessly or over a cabled connection, to a remote system, memory storage, and/or smart phone, for example. The ED 104 can be referred to as a non-implanted or a non-implantable subsystem. In some embodiments, the system 100 thus includes both an implantable subsystem and at least one non-implantable subsystem. While the ED 104 is described primarily in the context of providing the point of care (POC) to the patient at their home or other location remote from a medical facility, in other embodiments the ED 104 can be located in a medical facility.

One or more of the external electrodes 106 are external with respect to skin surface of a patient 101 and facilitate the bi-directional communication via conductive communication signals. For example, the external electrodes 106 are held proximate to a patient's skin and sense conductive communication signals transmitted by the IMD 102. At least one of the external electrodes 106 has a dielectric layer or dielectric barrier (not shown), herein referred to generally as "dielectric", positioned between an active surface of the external electrode 106, wherein the active surface can be metallic, made of a metal, and/or contain some metal component, and the patient's skin, forming a non-contact capacitively coupled interface that is sensitive to conductive communication signals from the IMD 102. For example, the capacitive connection may have no direct current (dc) pathway (e.g., purely capacitive).

As discussed further below, sense vectors between pairs of the external electrodes 106 are evaluated to identify the best and/or largest conductive communication signal. For example, in some embodiments when the IMD 102 is an LP, the IMD 102 can operate as a dipole (e.g., transmitting and receiving from therapeutic electrodes located at opposite ends as discussed in FIG. 3). Therefore, a sense vector associated with a set of the external electrodes 106 that are aligned to be proximate either side of the IMD 102 when the IMD 102 is substantially vertically implanted may result in an insufficient signal differential. An improved signal can be sensed, in some cases, by choosing one of the external electrodes 106 that are positioned further from the heart.

In some embodiments, the external electrodes 106 can be provided in one or more user-wearable garments and/or devices (e.g., shirt, pants, shorts, bra, watch, or other garment), a blanket, weighted blanket, a pillow, and/or any combination of products as discussed further below in FIG. 8. For example, the dielectric can be one or more of cotton, polyester or other synthetic, polymer, a polymer encapsulated product, and/or a non-metallic material, but is not so limited. In some cases, a dielectric such as a fabric can be approximately 250-500 microns thick.

Although the ED 104 is shown as fully separate from the patient 101 and the external electrodes 106, the ED 104 can be held within a form factor such as a garment, blanket, pillow, and the like that are discussed further below. The ED 104 and the external electrodes 106 can communicate wirelessly and/or through wired connections. In some embodiments, an additional communications device (not shown), such as a transceiver, may be included within a form factor and may communicate with the external electrodes 106 wirelessly or through wired connections. The transceiver may transmit the bi-directional communications between the external electrodes 106 and the ED 104 in real-time.

In some embodiments, the ED 104 can transmit data using Bluetooth protocol to the smart phone, allowing the patient 101 or other user to obtain active feedback from the various stages of data collection. For example, an application on the smart phone can confirm that the external electrodes 106 are sensing conductive communication signals and advise a status of data collection (e.g., in-process, complete, ongoing, failed, disconnected, etc.). The application can also send alerts to the patient 101 and/or the health care system based on the conductive communication data. Nightly alert monitoring can also be accomplished by the system 100 while the patient sleeps, such as through one or more of a garment, blanket, or pillow.

The ED 104 can be a bedside monitor or personal advisory module (PAM), or can be a smartphone, a tablet computer, a personal data assistant (PDA), a laptop computer, a desktop computer, or some other computing device that is capable of performing wireless and/or wired communication, such as in real-time. The ED 104 can thus include other programs and/or other applications, which can be referred to as apps. In some embodiments, the data obtained by the ED 104 from the IMD 102 can be used/processed by a software application executed by the ED 104.

Accordingly, the ED 104 and external electrodes 106 provide the technical advantage of simplifying data collection from the IMD 102, and in some cases can operate over an extended period of time without active input from the patient 101. Additionally, the ED 104 can automatically configure the external electrodes 106 to collect an optimal signal without input from the patient 101.

Figure 1B:
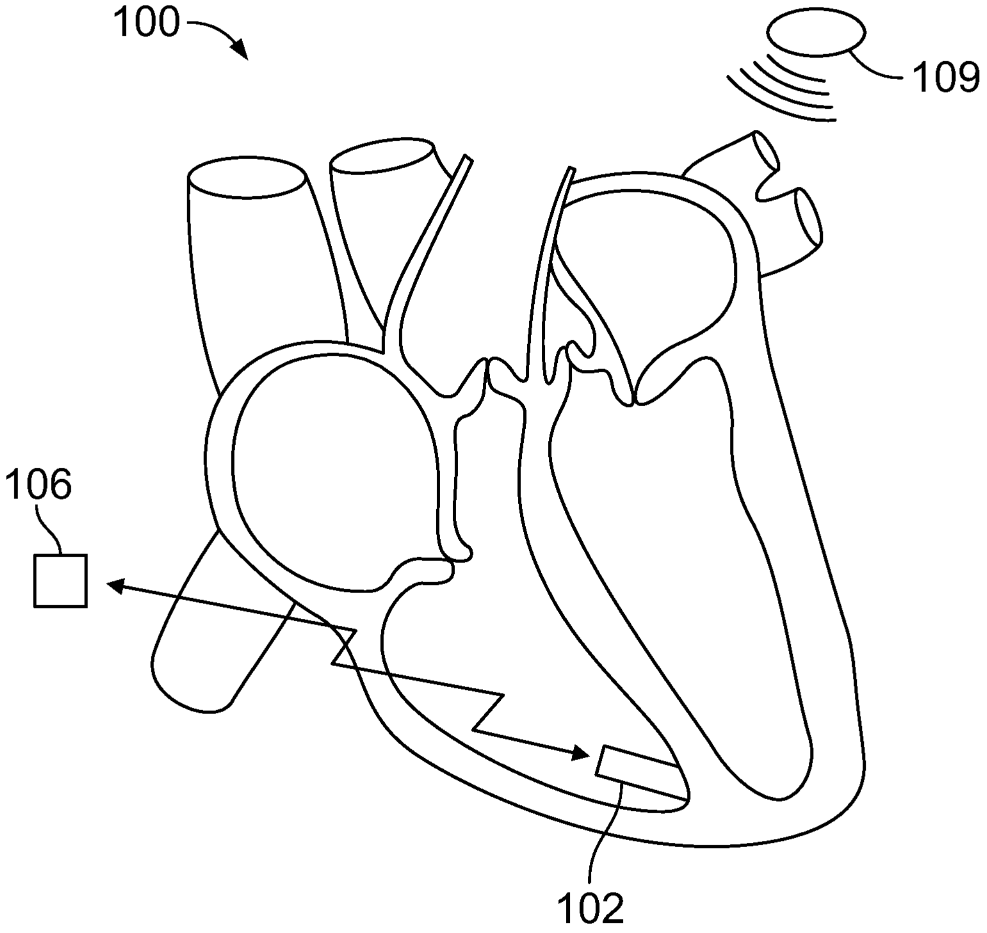
FIG. 1B illustrates an exemplary cardiac location at which a leadless pacemaker (LP) can be implanted within the heart.

FIG. 1B illustrates an exemplary cardiac location at which the IMD 102, introduced in FIG. 1A, can be implanted within the heart. In FIG. 1B the IMD 102 is located in a right ventricle but is not so limited. In some embodiments, one or more IMD 102 can be co-implanted with an implantable cardioverter-defibrillator (ICD) or implantable medical device (IMD) 109. In this example, the IMD 102 uses two or more therapeutic electrodes located within, on, or within a few centimeters of the housing of the IMD 102, for pacing and sensing at the cardiac chamber, and for bidirectional communication with the ED 104, and/or the IMD 109.

In some embodiments, the IMD 102 communicates with another IMD or LP (not shown) and with the IMD 109 by conductive communication through the same therapeutic electrodes that are used for sensing and/or delivery of pacing therapy. The IMD 102 also communicates by conductive communication through the therapeutic electrodes with the ED 104 via the capacitively coupled external electrodes 106. When conductive communication is maintained through the same therapeutic electrodes as used for pacing, the system 100 may omit an antenna or telemetry coil in the IMD 102. In some embodiments, the external electrodes 106 can transmit encoded information from the ED 104 to the IMD 102 or other IMD(s) 109 using, e.g., a modulated signal at a medium frequency of 10 kHz to 100 kHz, or in some cases approximately 100 kHz and higher. In other embodiments, the frequency can be approximately 50 kHz or higher, approximately 250 kHz, approximately 500 kHz, and/or approximately 1 MHz and higher. Also, the external electrodes 106 can be used to receive information from the IMD 102 or other IMD(s) 109 by detecting encoded information, which may or may not be included together with the pacing pulses of the IMD 102 or other type of pacemaker.

While the methods and systems described herein include examples primarily in the context of LPs, it is understood that certain methods and systems herein may be utilized with various other external and implanted devices. By way of example, the systems and methods of the present technology described herein may include and/or be used with other types of implantable medical devices (IMDs) implanted in a human, not just LPs. Examples of such other types of IMDs, with which embodiments of the present technology can be used, include a subcutaneous ICD (subQ ICD), BGA devices, as well as a more conventional type of pacemaker and/or ICD that includes a housing implanted in a pectoral region with leads having electrodes implanted within a patient's heart. Another type of IMD with which embodiments of the present technology can be used include an implantable cardiac monitor (ICM) that does not provide any therapy. These are just a few examples which are not intended to be all encompassing. For much of the following discussion, the IMD will be assumed to be an LP. However, as just mentioned above, embodiments of the present technology can be used with alternative types of IMDs that are configured to perform conductive communication with one or more non-implanted device(s), such as the ED 104.

Exemplary Leadless Pacemaker

Figure 2:
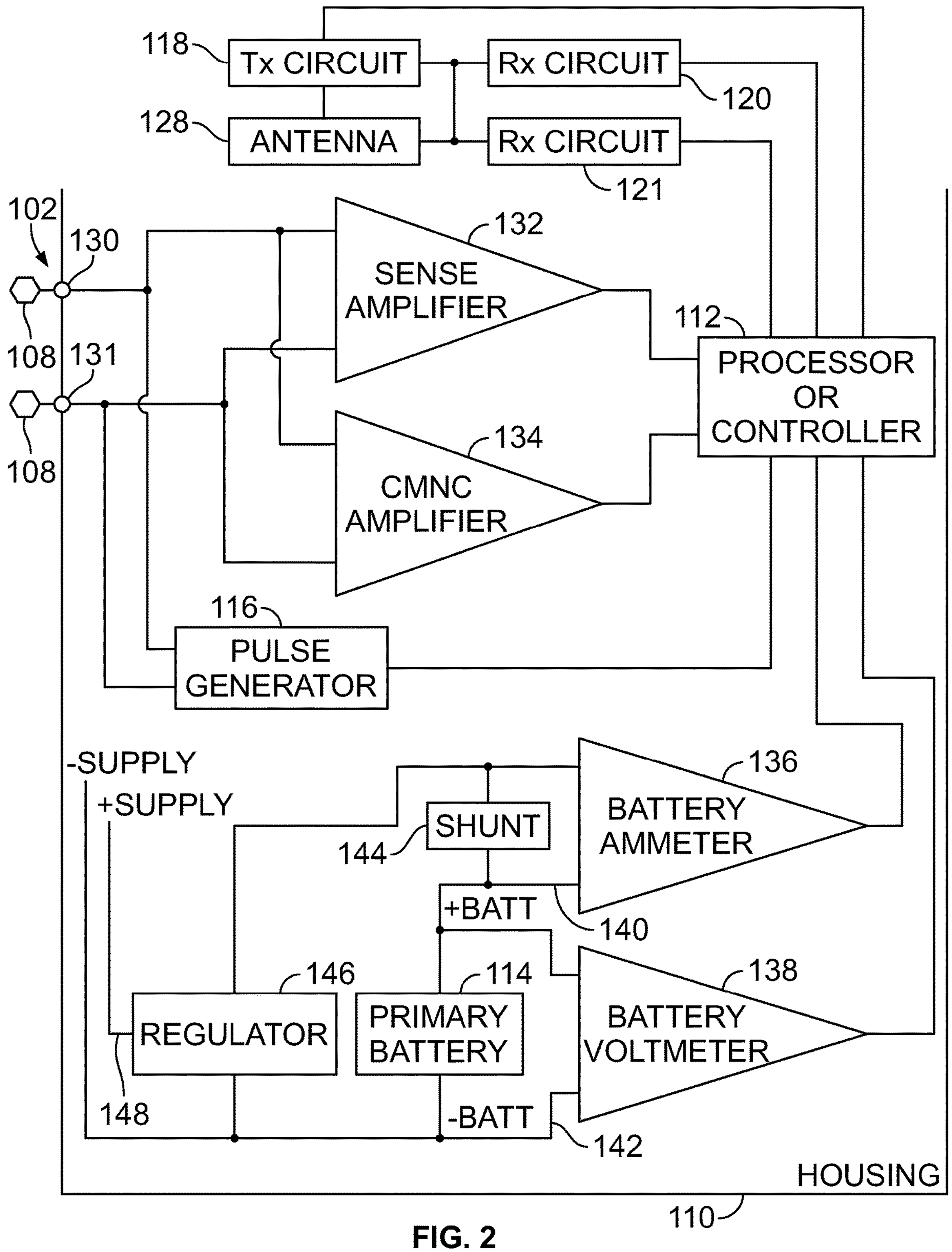
FIG. 2 is a pictorial diagram showing an embodiment for portions of the electronics within an LP configured to provide conductive communication through therapeutic electrodes in accordance with embodiments herein.

Referring to FIG. 2, a pictorial diagram shows an embodiment for portions of the electronics within the IMD 102 configured to provide conductive communication through the sensing/pacing electrodes (e.g., therapeutic electrodes) in accordance with embodiments herein. The IMD 102 comprises at least two leadless therapeutic electrodes 108 configured for delivering cardiac pacing pulses, sensing evoked and/or natural cardiac electrical signals, and performing uni-directional or bi-directional conductive communication. As noted above, the IMD 102 is an example of an IMD that can perform conductive communication, and more specifically, can transmit and receive conductive communication signals.

In certain embodiments, the IMD 102 includes a transmitter 118 and first and second receivers 120 and 121 that collectively define separate first and second communication channels (among other things) between the IMD 102 and the ED 104. Although first and second receivers 120 and 121 are depicted, in other embodiments, IMD 102 may include only first receiver 120, or may include additional receivers other than first and second receivers 120 and 121. The IMD 102 may also include one or more transmitters in addition to transmitter 118. In certain embodiments, the IMD 102 may communicate over more than just first and second communication channels. In certain embodiments, the IMD 102 may communicate over one common communication channel. In accordance with certain embodiments, the IMD 102 may communicate conductively over a common physical channel via the same therapeutic electrodes 108 that are also used to deliver pacing pulses. Usage of the therapeutic electrodes 108 for conductive communication enables the IMD 102 to perform antenna-less and telemetry coil-less communication. In other embodiments, wireless transceivers, communication coils, and/or an antenna 128 can be used to facilitate communication between the IMD 102 and the IMD 109, and/or between the IMDs 102, 109 and/or the ED 104.

Conductive communication messages may be formatted in various manners. As one example, each communications message may include a leading trigger pulse followed by a time gap and then information (e.g., data packet(s)). The trigger pulse is transmitted over a first channel (e.g., with a desired pulse duration and/or within a fundamental frequency range). The trigger pulse indicates that one or more data packets and/or communications messages is/are about to be transmitted over the same or a second channel (e.g., within a higher frequency range). The data packet(s) and/or communications message(s) can then be transmitted over the first or second channel.

The data packet(s) may include various types of data, such as data indicative of one or more events (e.g., a sensed intrinsic atrial activation for an atrial located LP, a sensed intrinsic ventricular activation for a ventricular located LP). The data packet(s) may include different markers for intrinsic and paced events. The data packet(s) may also indicate start or end times for timers (e.g., an AV interval, a blanking interval, etc.). Additionally, or alternatively, the data packet(s) may include stored EGM data, device status information, fault information and any other type of data communicated to/from an ED 104 and/or IMD 109 as described in the various patents and applications referenced herein. Optionally, the data packet and/or communications message may include a message segment that includes additional/secondary information.

Optionally, the ED 104 that receives any implant to external (i2e) communication from implanted device such as the IMD 102 (or other IMD 109) may transmit a receive acknowledgement indicating that the receiving ED 104 received the i2e communication, etc. Where an i2e communication is performed using conductive communication, the i2e communication can be referred to more specifically as i2e conductive communication, or more generally as conductive communication.

In accordance with certain embodiments herein, the pulse widths and other transmit/receive parameters may be adjusted to achieve a desired total (summed) current demand from both transmitter 118 and receivers 120 and 121. The transmitter current decreases nearly linearly with narrowing bandwidth (pulse width), while a relation between receiver current and bandwidth is non-linear.

In accordance with certain embodiments herein, the ED 104 may communicate over an ED-to-LP channel, with IMD 102 utilizing the same communication scheme. The ED 104 may listen to the event message that may be transmitted, for example, between IMD 102 and IMD 109, such that ED 104 does not transmit communication signals until after an implant to implant (i2i) messaging sequence is completed.

In accordance with certain embodiments, IMD 102 may combine transmit operations with therapy. A transmit event marker may be configured to have similar characteristics in amplitude and pulse width to a pacing pulse and IMD 102 may use the energy in the event messages and/or communications messages to help capture the heart.

The IMD 102 may be programmable such as to afford flexibility in adjusting pulse widths, amplitudes, and the like. In some embodiments, different receiver circuits may be provided and selected for certain pulse widths, where multiple receivers may be provided on a common ASIC, thereby allowing the user to vary the parameters in an IMD 102 after implant.

In some embodiments, the IMD 102 can comprise a hermetic housing 110 configured for placement on or attachment to the inside or outside of a cardiac chamber and at least two leadless therapeutic electrodes 108 proximal to the housing 110 and configured for bidirectional communication with at least one other device, within or outside the body, such as the ED 104.

Accordingly, FIG. 2 depicts the IMD 102 and shows the LP's functional elements substantially enclosed in the hermetic housing 110. The IMD 102 has at least two therapeutic electrodes 108 located within, on, or near the housing 110, for delivering pacing pulses to and sensing electrical activity from the muscle of the cardiac chamber, and for bidirectional communication with at least one other device within or outside the body, such as the ED 104. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the therapeutic electrodes 108, circuits 134 for receiving information from at least one other device (e.g., ED 104) via the therapeutic electrodes 108, and a pulse generator 116 for generating pacing pulses for delivery via the therapeutic electrodes 108 and also for transmitting information to at least one other device (e.g., ED 104) via the therapeutic electrodes 108. The housing 110 can further contain circuits for monitoring device health, for example a battery current monitor 136 and a battery voltage monitor 138, and can contain circuits for controlling operations in a predetermined manner.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the IMD 102. The shunt 144 enables the battery current monitor 136 to provide the processor 112 with an indication of battery current drain and indirectly of device health. The illustrative power supply can be a primary battery 114.

In various embodiments, IMD 102 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

Figure 3:
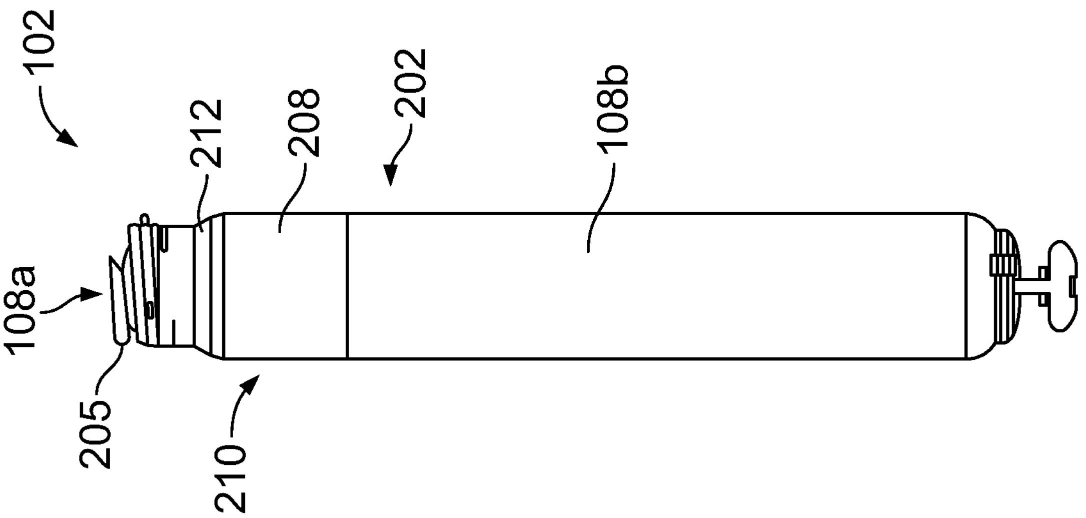
FIG. 3 shows an LP in accordance with embodiments herein.

FIG. 3 shows an IMD 102. The IMD 102 can include a hermetic housing 202 with therapeutic electrodes 108*a* and 108*b* disposed thereon. As shown, therapeutic electrode 108*a* can be separated from but surrounded partially by a fixation mechanism 205, and the therapeutic electrode 108*b* can be disposed on the housing 202. The fixation mechanism 205 can be a fixation helix, a plurality of hooks, barbs, or other attaching features configured to attach the pacemaker to tissue, such as heart tissue.

The housing 202 can also include an electronics compartment 210 within the housing 202 that contains the electronic components necessary for operation of the pacemaker, including, for example, a pulse generator, communication electronics, a battery, and a processor for operation. The hermetic housing 202 can be adapted to be implanted on or in a human heart, and can be cylindrically shaped, rectangular, spherical, or any other appropriate shapes, for example.

The housing 202 can comprise a conductive, biocompatible, inert, and anodically safe material such as titanium, 316L stainless steel, or other similar materials. The housing 202 can further comprise an insulator disposed on the conductive material to separate therapeutic electrodes 108*a* and 108*b*. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between therapeutic electrodes 108*a* and 108*b*. In some embodiments, the housing 202 itself can comprise an insulator instead of a conductor, such as an alumina ceramic or other similar materials, and the electrodes can be disposed upon the housing.

As shown in FIG. 3, the IMD 102 (e.g., pacemaker) can further include a header assembly 212 to isolate therapeutic electrodes 108*a* and 108*b*. The header assembly 212 can be made from PEEK, tecothane or another biocompatible plastic, and can contain a ceramic to metal feedthrough, a glass to metal feedthrough, or other appropriate feedthrough insulator as known in the art.

The therapeutic electrodes 108*a* and 108*b* can comprise pace/sense electrodes or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, therapeutic electrode 108*a* can be a pace/sense electrode and therapeutic electrode 108*b* can be a return electrode. The therapeutic electrode 108*b* can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the therapeutic electrode 108*a* in FIG. 3) into contact with stimulable tissue. Therapeutic electrode 108*b* can serve as an indifferent electrode for sensing and pacing. The fixation mechanism 205 may be coated partially or in full for electrical insulation, and a steroid-eluting matrix may be included on or near the device to minimize fibrotic reaction, as is known in conventional pacing electrode-leads.

Exemplary Communication Pathway Between LP (and/or IMD) and External Device

The IMD 102, or more generally one or more IMDs or LPs, can communicate with at least one ED 104 via conductive communication. Conductive communication, which is sometimes also known as Intra-Body Communication (IBC) or Body Channel Communication (BCC), is a non-RF wireless data communication technique that uses the human body itself as the communication channel or transmission medium. Such communication may take place via communication pathways comprising a receiving pathway that decodes information encoded on pulses generated by one or more of the IMDs (e.g., IMD 102) and conducted through body tissue to the external electrodes 106 that are capacitively coupled to the patient (e.g., to the skin of the patient or through a dielectric to the skin of the patient). According to the illustrative arrangement, the communication pathways can be configured for communication with the IMD 102 via two or more therapeutic electrodes 108*a* and 108*b* and conduction through body tissue. A technical advantage of at least some embodiments is the use of at least some external electrodes 106 that form the non-contact capacitively coupled interface between the ED 104 and the patient, eliminating the skin to electrode impedance variability experienced when interfacing directly with the patient's skin (e.g., oil on skin, hair, dry skin, wet skin, etc.).

The ED 104 includes at least two external electrodes 106 that are configured to be held proximate to the skin of the patient. In accordance with certain embodiments, the ED 104 is connected by at least one communication transmission channel and has receiving functional elements for receiving encoded information from the IMD 102 and/or IMD 109 via the external electrodes 106. From the point of the skin, the communication transmission channel within the body is wireless, includes the ion medium of the intra- and extra-cellular body liquids, and enables electrolytic-galvanic coupling between the external electrodes 106 and the IMD 102.

In accordance with certain embodiments, information transmitted between the IMD 102 and the ED 104 can be conveyed by modulated signals at the approximate range of 10 kHz to 100 kHz which is a medium-high frequency, or at higher frequencies, such as greater than 100 kHz (e.g., approximately 250 kHz, approximately 500 kHz, and/or approximately 1 MHz). In some embodiments the frequency range can be up to approximately 2 MHz. The signals are passed through the communication transmission channel by direct conduction. A modulated signal in the frequency range has a sufficiently high frequency to avoid any depolarization within the living body which would lead to activation of the skeletal muscles and discomfort to the patient. In addition, the frequency of the modulated signal is high enough such that the non-contact capacitively coupled interface between the patient's skin and the external electrode 106, including the dielectric layer therebetween, renders the capacitance of the dielectric substantially "invisible". The frequency is also low enough to avoid causing problems with radiation, crosstalk, and excessive attenuation by body tissue. Thus, information may be communicated at any time, without regard to the heart cycle or other bodily processes.

In some embodiments, the IMD 102 can generate cardiac pacing pulses and encode information onto the generated cardiac pacing pulses by selective alteration of pacing pulse morphology that is benign to therapeutic effect and energy cost of the pacing pulse. The cardiac pacing pulses conduct into body tissue via the therapeutic electrodes 108 for antenna-less and telemetry coil-less communication. In some cases, for information transmitted from the IMD 102 to the ED 104, a communication scheme can be used in which the information is encoded on one or more pacing pulses. The pulse morphology is altered to contain the encoded information without altering the therapeutic benefits of the pacing pulse. The energy delivered by the pacing pulse remains essentially the same after the information is encoded. The ED 104 receives the pacing pulses through the associated external electrodes 106. Encoded information is drawn from one or more pacing pulses and can contain various types of information, including an indication of when a ventricular depolarization occurred.

The IMD 102 can be configured to detect a natural cardiac depolarization, time a selected delay interval, and deliver an information-encoded pulse during a refractory period following the natural cardiac depolarization. By encoding information in a pacing pulse, power consumed for transmitting information is not significantly greater than the power used for pacing. Information can be transmitted through the communication channel with no separate antenna or telemetry coil. In some embodiments, communication bandwidth is low with only a small number of bits encoded on each pulse.

Alternatively or in addition to encoding information in gated sections and/or pulse intervals, overall pacing pulse width can be used to encode information. Non-pacing pulses can additionally or alternatively be used to transmit conductive communication signals.

The illustrative ED 104 and associated operating methods or techniques enable presentation to a user of information gathered from the IMD 102 and/or other IMD(s) using conductive communication. Some of the information to be presented may include battery voltage, lead impedance, electrocardiogram amplitude, or current drain of the device. The information can be presented to a user on a display screen. Some embodiments or configurations of the ED 104 can include a secondary link, for example either wireless or through a cable, to another display device, such as a hand-held computer, smart phone, or terminal. The secondary link can also include communication over a local area network or the internet for display at a remote terminal.

Event Messaging

Figure 4:
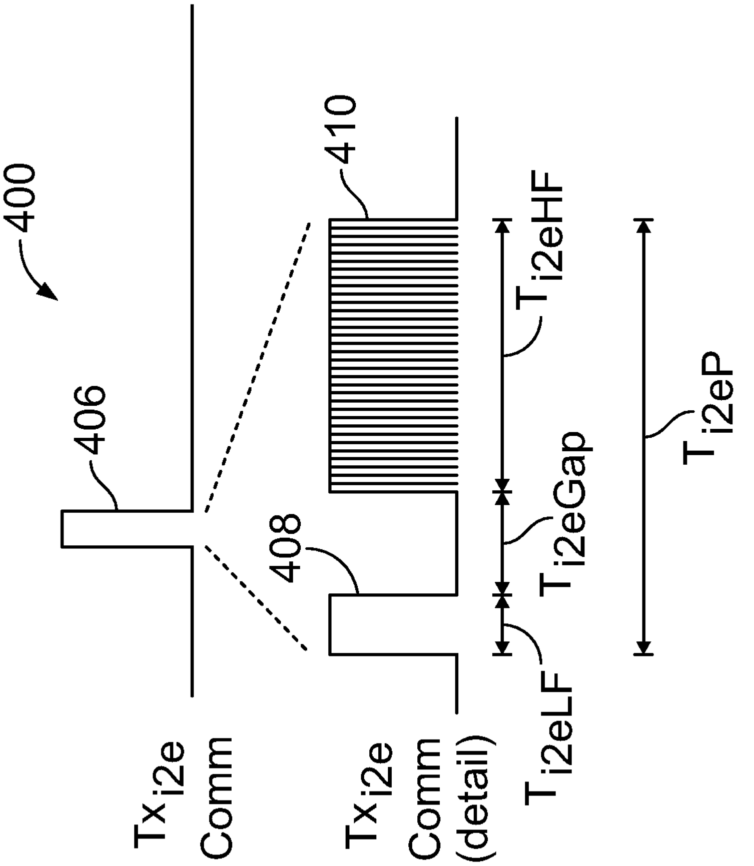
FIG. 4 is a timing diagram demonstrating one embodiment of implant to external (i2e) communication, and more generally, is a timing diagram for an exemplary conductive communication signal in accordance with embodiments herein.

FIG. 4 is a timing diagram demonstrating one embodiment of implant to external (i2e) communication, and more generally, is a timing diagram for an exemplary conductive communication signal in accordance with embodiments herein. The i2e communication may be transmitted, for example, from IMD 102 to the ED 104, and the communication scheme revolves around bit representation that is a biphasic waveform. The i2e transmission 400 includes an envelope 406 that may include one or more individual pulses. For example, in this embodiment, envelope 406 includes a low frequency pulse 408 (e.g., a first pulse) followed by a high frequency pulse train 410. Low frequency pulse 408 lasts for a period $T_{i2eLF}$, and high frequency pulse train 410 lasts for a period $T_{i2eHF}$. The end of low frequency pulse 408 and the beginning of high frequency pulse train 410 are separated by a gap period, $T_{i2eGap}$. The transmission 400 is an example of a conductive communication signal.

The high frequency pulse train 410 can be used to transmit and receive information to and from the ED 104, such as a communications message. In some embodiments, the ED 104 will prepare and transmit a response (e.g., an e2i transmission that can be a communications message transmitted within the conductive communication signals) to the IMD 102 within a predetermined window of time, such as within approximately 30 microseconds etc.

The conductive communication signal experiences a delay as the signal propagates through different media. Capacitively coupling one or more of the external electrodes 106 through a known dielectric or dielectric layer (e.g., medium) allows for greater timing control for transmit and receive. For example, a delay of the conductive communication signal, such as the i2e signal sent by the IMD 102, is less variable and more controllable compared to a delay using coupling of a metal electrode to skin directly which is subject to the variabilities of patient skin connection, moisture content of skin, etc. Therefore, the ED 104 can, in some cases, assume a fixed or relatively fixed delay of signal based at least in part on the dielectric. Accordingly, an advantage of forming the non-contact capacitively coupled interface between the patient's skin and the external electrode 106 that includes the dielectric layer therebetween is that material, distance, and area associated with the interface are known or can be reliably estimated.

As shown in FIG. 4, the i2e transmission 400 lasts for a period $T_{i2eP}$. A delay period can separate successive i2e transmissions 400 and/or additional communications (e.g., pulses) may be included. In some embodiments, if the i2e transmission 400 is sent together with a pace pulse (not shown), the end of the i2e transmission 400 and the beginning of the pace pulse can be separated by a delay period.

In accordance with some embodiments, communication between the IMD 102 and ED 104 is implemented via conductive communication of, for example, commands and information in the pulse train 410 (per i2e communication protocol). Conductive communication can be transmitted from the therapeutic electrodes 108 at frequencies outside the RF or Wi-Fi frequency range. Alternatively, the conductive communication may be conveyed over communication channels operating in the RF or Wi-Fi frequency range.

Figure 5:
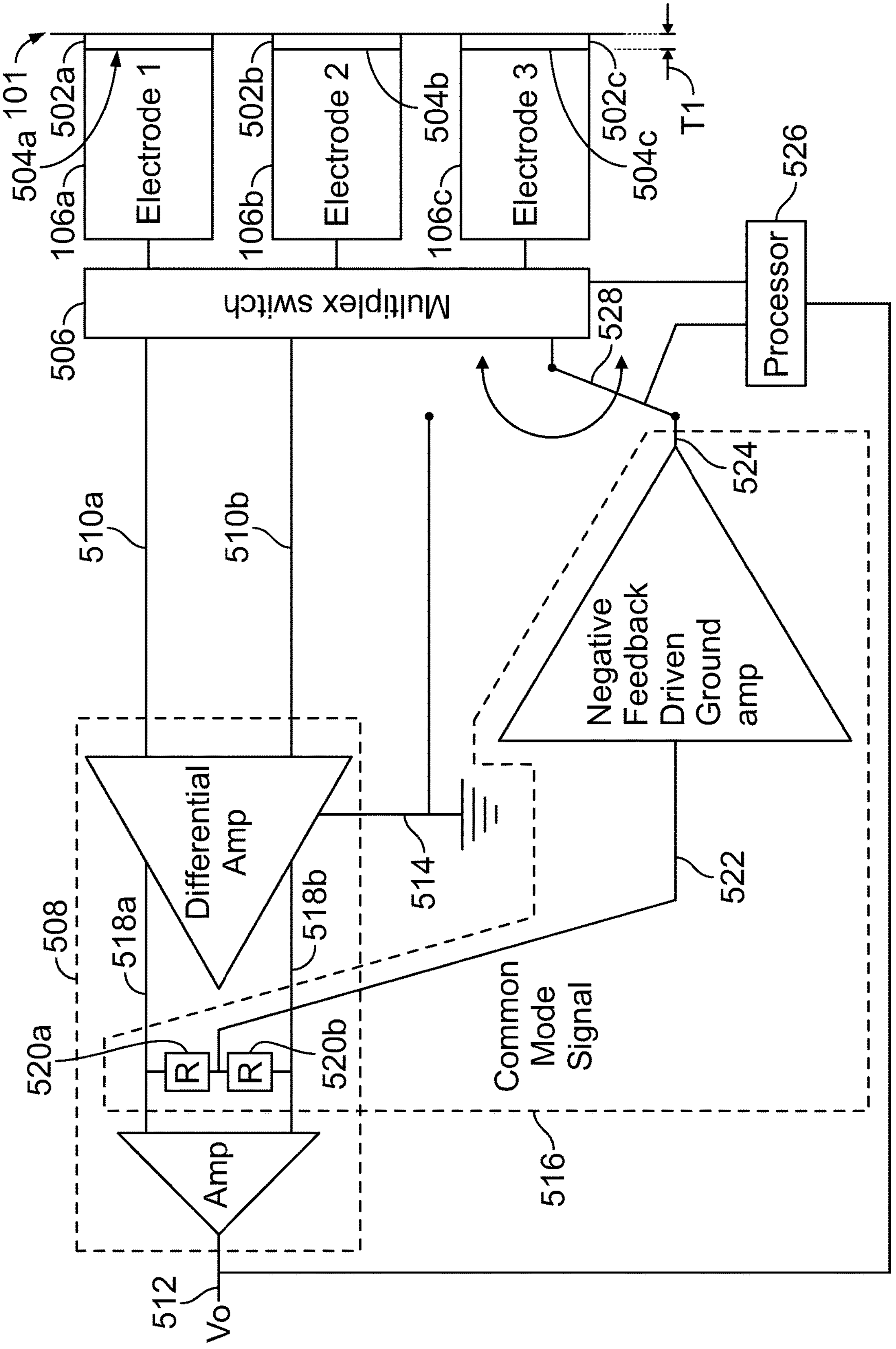
FIG. 5 is a pictorial diagram showing an embodiment for portions of the electronics within the ED configured to sense signals received by the external electrodes and to select a configuration of the external electrodes in accordance with embodiments herein.

Circuitry for Sensing Conductive Communication Signals and Selecting Configuration of External Electrodes FIG. 5 is a pictorial diagram showing an embodiment for portions of the electronics within the ED 104 configured to sense signals received by the external electrodes 106 and to select a configuration of the external electrodes 106 in accordance with embodiments herein. The circuitry shown is receive only; however, transmit circuitry is discussed further below in FIG. 7 and would, in some examples, utilize the same external electrodes 106 selected for receiving.

As discussed previously, the external electrodes 106 are capacitively coupled to the patient 101. Each of the external electrodes 106 (e.g., 106*a*, 106*b*, 106*c*) is shown with a corresponding dielectric layer 502 (e.g., 502*a*, 502*b*, 502*c*) between a surface 504 (e.g., 504*a*, 504*b*, 504*c*), for example a metal surface, of the corresponding external electrode 106 and the skin of the patient 101. The dielectric has a known or estimated thickness T1 that spaces the associated external electrode 106 apart from the patient's skin to form a non-contact capacitively coupled interface between the patient's skin and the external electrode 106. The non-contact capacitively coupled interface passes the conductive communication signals and can filter certain frequencies or range(s) of frequencies. For example, the non-contact capacitively coupled interface can pass conductive communication signals with a frequency of at least 100 kHz and block, or at least partially attenuate, signals below 100 kHz. In other embodiments, the passed and blocked/attenuated frequency ranges can be different. Although the dielectric layers 502*a*, 502*b*, and 502*c* are shown as separate and distinct portions, the dielectric layers 502 can all be portions of a substantially contiguous material, such as fabric of a shirt, blanket, pants, etc. In other embodiments, less than a total number of the external electrodes 106 used to sense the conductive communication signals include(s) the dielectric layer 502. For example, one or two of the external electrodes 106 can instead be in direct contact with the skin of the patient 101.

Figure 7:
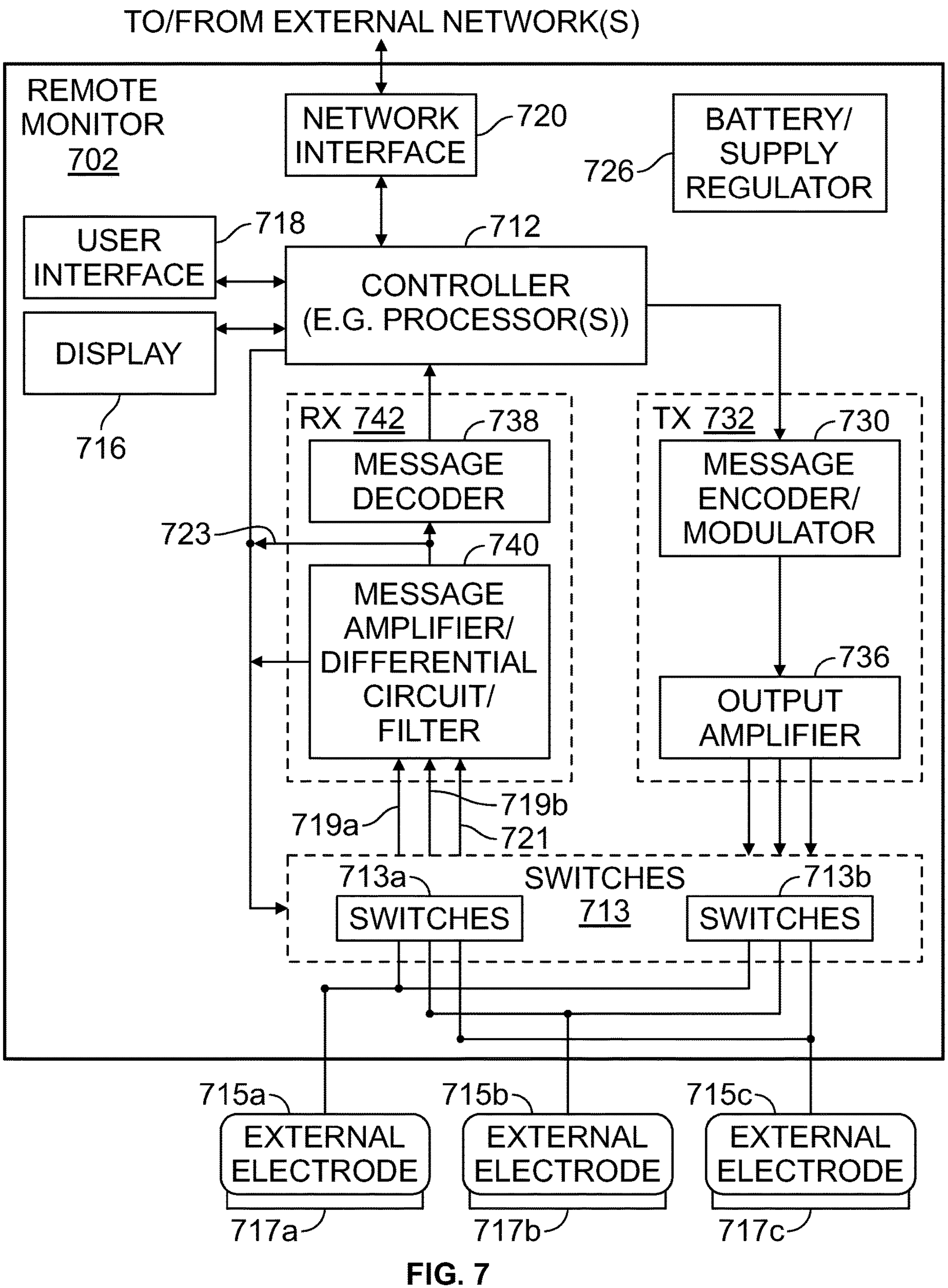
FIG. 7 is a block diagram illustrating an exemplary remote monitor in accordance with embodiments herein.

The circuitry within FIG. 5, as well as the external electrodes 106 and other processing/circuitry within FIG. 7, are capable of switching between transmit and receive within a short time window in order to transmit a response from the ED 104 to the IMD 102 in the next timing window as discussed previously in FIG. 2. For example, although the conductive communication signals is/are transmitted through a capacitive medium (e.g., dielectric, skin, and the like), which are also a capacitive signal conditioner, the elements within the ED 104 and external electrodes 106 are capable of high-speed processing.

For example, in some embodiments a delay of signal is experienced as the conductive communication signals propagate from the IMD 102 to the ED 104, and from the ED 104 to the IMD 102, particularly moving through the capacitively coupled medium (e.g., the dielectric layer 502). In contrast to the variations of patient's skin and the skin to electrode impedance when all of the electrodes directly contact the skin, such as with gel, etc., the system disclosed herein eliminates the variable of the skin-to-metal or skin-to-electrode connection that is not controlled due to patient skin variabilities (e.g., skin moisture content, hair, etc.). The signal propagation delay in the disclosed system herein can be controlled by applying assumptions based on, for example, dielectric constant of material such as fabric (e.g., a patient's clothing), distance between the active surface of the external electrode and the patient skin based on an expected thickness T1 of the patient's clothing or thickness T1 of another provided form factor, as well as the size of the associated external electrode 106. Accordingly, such factors may be taken into consideration when designing the form factor.

In some embodiments, the external electrodes 106 are in communication with a switching block 506, such as a multiplexor, that can include a set of switches and/or switching logic (not shown) associated with each external electrode 106. The configuration of the switches within the switching block 506 determines which two of the external electrodes 106 are used for conductive communication, and which one of the electrodes 106 provides ground. Although only three external electrodes 106 are shown, in some embodiments, more than three external electrodes 106 can be sensed and appropriate switches and switching logic can be applied to select the desired external electrodes 106 as discussed below.

Two of the external electrodes 106 (e.g., sensing electrodes) are connected to a two-stage differential circuit 508 that amplifies input signals 510*a*, 510*b* from the external electrodes 106, detects a potential difference between the signals, and outputs a differential signal 512, such as a voltage level, that represents the difference between the input signals 510*a*, 510*b*. Therefore, the differential signal 512 corresponds to the conductive communication signals sensed by the external electrodes 106. Other circuitry may be used to output the differential signal 512 and may include additional components such as filters (not shown). Further, the differential signal 512 can be processed to identify a communications message transmitted from the ED 104 within the conductive communication signals.

In some embodiments, one of the external electrodes 106 is tied to passive ground, such as ground potential 514 of the ED 104 and/or elements within the ED 104. Therefore, the grounded contact keeps the patient 101 at the same voltage potential as the ED 104.

Common mode signals can be present in the patient 101 due to household/building electrical signals (e.g., approximately 60 Hz in the United States) and result in noise in the signals sensed by the external electrodes 106. Therefore, in other embodiments, a feedback circuit 516 drives an active ground for common mode rejection back into the patient 101 through the capacitively coupled interface. As a result, the common mode rejection signal is continuously or near-continuously adjusted based on the input signals 510*a*, 510*b*. In this example, signals 518*a*, 518*b* output from a first stage of the differential circuit 508 are tied together, such as with resistors 520*a*, 520*b*, and common mode signal 522 is inverted and/or shifted out of phase before being passed to the external electrode 106 configured as the ground contact. Common mode rejection signal or feedback signal 524 is driven into the patient 101 through, in some embodiments, the dielectric layer 502. The feedback signal 524 at least partially removes and/or cancels the common mode component (e.g., noise or frequency caused by the common mode signal) that is within the patient 101. Accordingly, the common mode signal 522 is being measured, adjusted, and at least partially canceled by driving the ac feedback signal 524 through the highly capacitive layer into the patient 101.

A controller or processor 526 can control a switch 528 to switch between passive ground (e.g., connected to ground potential 514) and active or driven ground (e.g., connected to feedback circuit 516) to form a passive or driven grounding node to the patient's skin with the ground electrode. The processor 526 can also be in communication with the switching block 506 and monitor the differential signal 512 to configure the external electrodes 106.

In some embodiments, the processor 526 may configure the switching block 506 to compare the differential signals 512 for each of the possible combinations of the external electrodes 106 (e.g., external electrodes 106*a*, 106*b* as sensing contacts and external electrode 106*c* as ground contact, external electrodes 106*b*, 106*c* as sensing contacts and external electrode 106*a* as ground contact, external electrodes 106*a*, 106*c* as sensing contacts and external electrode 106*b* as ground contact, etc.) to identify the largest output voltage level Vo (e.g., differential signal 512). The processor 526 may evaluate the configurations with the passive ground and the configurations with the driven ground. Additional external electrodes 106 can be provided within the garment or other form factor and can also be evaluated to identify the configuration that provides a greatest differential signal 512.

In other embodiments, the processor 526 can compare the differential signal 512 of a first configuration of the external electrodes 106 to a threshold level. In some cases, if the differential signal 512 exceeds the threshold level, the processor 526 maintains the configuration. If the differential signal 512 is lower than the threshold level, the processor 526 can reconfigure the external electrodes 106 to a different configuration until an acceptable configuration is identified. In still further embodiments, the processor 526 may default to the previous configuration and/or always start the comparison process with a predetermined configuration.

Figure 6A:
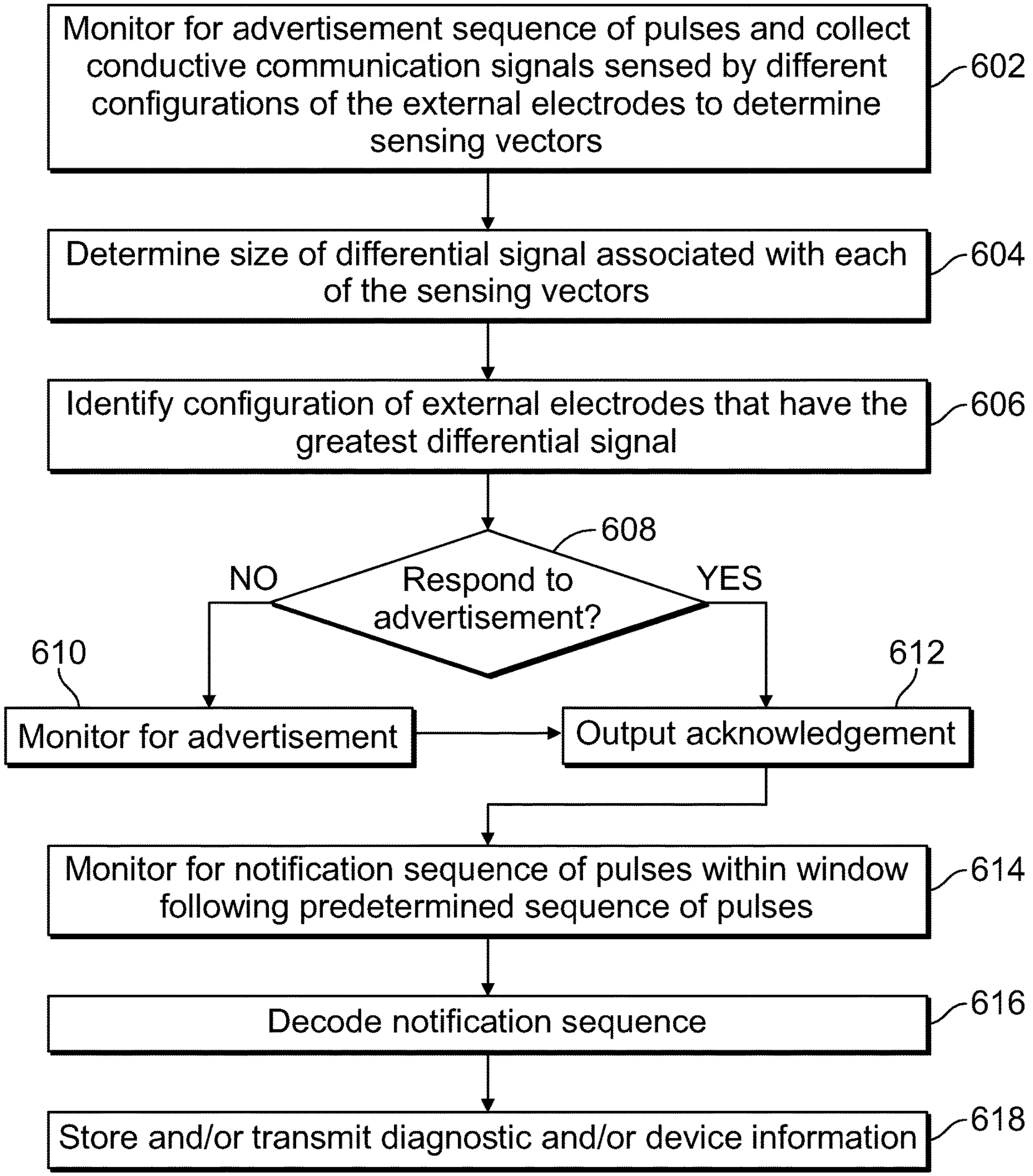
FIG. 6A illustrates a method for selecting a configuration of the external electrodes and establishing bi-directional communication between the LP and the ED in accordance with embodiments herein.

FIG. 6A illustrates a method for selecting a configuration of the external electrodes 106 and establishing bi-directional communication between the IMD 102 (or other IMD 109) and the ED 104 in accordance with embodiments herein. The operations of FIG. 6A may be implemented by hardware, firmware, circuitry and/or one or more processors housed partially and/or entirely within an ED 104 or IMD 102, 109, a local external device, remote server or more generally within a health care system. Optionally, the operations of FIG. 6A may be partially implemented by an IMD 102, 109 and partially implemented by a local external device, remote server or more generally within a health care system. For example, the IMD 102, 109 includes IMD memory and one or more IMD processors, while each of the external devices/systems (e.g., local, remote or anywhere within the health care system) include external device memory and one or more external device processors.

At 602, one or more processors monitor for conductive communication signals that include conductive communication pulses transmitted by the IMD 102 within the patient 101, such as by using a plurality of different sensing vectors. For example, the ED 104 receives the advertisement pulse and/or sequence of pulses and the notification sequence of pulses and/or information encoded therein by the IMD 102 via the two or more external electrodes 106 that form capacitively coupled interfaces (e.g., non-contact or contact) with the patient's skin.

A sensing vector can generally be referred to a path extending between two or more of the external electrodes 106. For example, the one or more processors can monitor for an advertisement sequence of pulses using different configurations of the external electrodes 106. The conductive communication signals are sensed by configurations of the electrodes 106 that are in communication with the ED 104. The external electrodes 106 can be configured using, for example, the switching block 506 and ground switch 528 as shown in FIG. 5. In some embodiments, the first configuration includes the first and second external electrodes 106 as sense electrodes and connects the third external electrode 106 to either passive or active ground as a ground electrode (e.g., forming a passive or driven grounding node to the patient's skin), the second configuration includes the first and third external electrodes 106 as sense electrodes and connects the second external electrode 106 to either passive or active ground as the ground electrode, and the third configuration includes the second and third external electrodes 106 as sense electrodes and connects the first external electrode 106 to either passive or active ground as the ground electrode. In this example, there may be six configurations wherein half of the configurations connect one of the external electrodes 106 to passive ground 514 and the other half connects one of the external electrodes 106 to active or driven ground, indicated as feedback signal 524 in FIG. 5. It should be understood that a larger number of configurations can be identified and monitored if the system 100 includes more than three external electrodes 106.

If conductive communication signals are not detected, the ED 104 may determine that the external electrodes 106 are not capacitively coupled to the patient 101, not in communication with the ED 104, and/or that the IMD 102 is not transmitting. The one or more processors may repeat the monitoring at 602, such as after a period of time. In some embodiments, the ED 104 may display and/or transmit an error message to alert the patient 101 and/or monitoring system.

In general, at 602, the one or more processors monitor for a predetermined sequence of pulses known as the advertisement sequence of pulses which are periodically transmitted by the IMD 102. In accordance with certain embodiments, the advertisement sequence of pulses is a predetermined sequence of pulses that indicates to the ED 104 that an IMD 102 is implanted within a patient. The advertisement sequence of pulses can also be referred to as a sniff sequence of pulses, or more succinctly as a sniff. Further, in accordance with certain embodiments, in response to outputting the advertisement sequence of pulses, the IMD 102 monitors for an acknowledgement sequence of pulses within an acknowledgement window, to thereby enable the IMD 102 to determine whether an ED 104 is attempting to establish a communication session with the IMD 102. This monitoring can be referred to as active, wherein the term "active" indicates that the alert and/or notification sequence of pulses (which can be encoded with diagnostic information associated with the IMD 102 and/or associated with the patient 101 within which the IMD 102 is implanted) is sent in response to receiving acknowledgement type of feedback from the external device 104.

At 604, the one or more processors detect a potential difference, between the input signals 510 to determine a size of the differential signal 512 for each of the plurality of sensing vectors. It should be understood that other measures for each of the configurations can be used, such as a respective metric indicative of power and/or quality of a communication signal received from the IMD 102 using the configuration of external electrodes 106.

At 606, the one or more processors identify, in response to the results of 604, a configuration of the external electrodes 106 that provides the greatest differential signal. Therefore, the "best" sensing vector that has the largest differential signal as measured between the two external electrodes 106 designated as sense electrodes, is identified.

At 608, in some embodiments, the one or more processors may determine whether the ED 104 and the external electrodes 106 have adequate time to respond to the advertisement sequence of pulses. For example, as discussed previously, the protocol may require that a response be sent in the time window following the sniff. If too much time has elapsed while the configuration of external electrodes 106 is identified, the method passes to 610 where the one or more processors may continue to monitor for the next sniff with the selected configuration of external electrodes 106.

If the response can be provided in time (at 608) and/or when the sniff is detected at (610), flow passes to 612, where the one or more processors use the configuration of external electrodes 106 to output a remote monitor acknowledgement (ACK) sequence of pulses. This provides an indication to the IMD 102 that the ED 104 is proximate to the patient 101 with the external electrodes 106 forming capacitively coupled interfaces (e.g., at least one of the external electrodes 106 forming a non-contact capacitively coupled interface) with the skin of the patient 101.

With respect to the ACK sequence as well as other transmissions between the IMD 102 and the ED 104, the receipt, processing, and transmission occur within a short time, such that the ED 104 transmits in the next timing window (e.g., successive window) to be acknowledged properly and thus the IMD 102 can respond properly (e.g., establishing bi-directional communication). In some embodiments, the time between receiving the signal at the ED 104 and transmitting a response from the ED 104 to the IMD 102 is approximately 30 microseconds, but is not so limited.

At 614, the ED 104 monitors, using the identified configuration of external electrodes 106, for a further sequence of pulses (e.g., the notification sequence) within a window following the transmitted ACK, and determines whether a notification sequence is detected within the window. In some embodiments, the notification sequence can be the HF pulse train 410 following the LF pulse 408 as shown and discussed previously in FIG. 4. Also, the same sensing vector as identified at 606 is used to receive one or more conductive communication signals from the IMD 102.

In accordance with some embodiments, if the IMD 102 detects the ED 104 acknowledgement sequence of pulses within an acknowledgement monitor window, the IMD 102 can cooperate with the ED 104 to establish a bi-directional communication session with the ED 104. In other embodiments, the IMD 102 can output a subsequent notification sequence of pulses within one or more notification transmission window(s) following the outputting of the advertisement sequence of pulses. This notification sequence of pulses output by the IMD 102 can be encoded with diagnostic information associated with the IMD 102 and/or associated with the patient 101 within which the IMD 102 is implanted.

At 616, in response to the detection of the notification sequence sent by the IMD 102, the one or more processors decode the notification sequence of pulses detected within the window to identify diagnostic information, which includes one or more notification conditions encoded therein. The notification condition(s) can be associated with the IMD 102 and include, but are not limited to, a recommended replacement time (RRT) condition, a device reset condition, an end of service (EOS) condition, a high current condition, a memory region full condition, a memory corruption condition, a poor conductive communication condition, and the like. Alternatively, or additionally, the notification condition(s) can be associated with the patient 101 within which the IMD 102 is implanted, including but not limited to, an arrhythmia detection, a non-cardiac physiological condition detection, an increased pacing burden detection, an automatic mode switching (AMS) detection, a pacemaker mediated tachycardia (PMT) detection, a premature ventricular contraction (PVC) detection, and/or the like.

At 618, the one or more processors store within a memory and/or transmit to a patient care network the diagnostic information and/or raw data associated with the notification sequence of pulses and/or information decoded from the notification sequence of pulses received from the IMD 102 using the configuration of the external electrodes 106 identified at 606. More generally, the ED 104 stores and/or forwards data it obtained from one or more conductive communication signals received from an implanted IMD 102 using the identified sensing vector.

In other embodiments, the IMD 102 can passively communicate with the ED 104. The term "passive" indicates that the alert is sent by the IMD 102 without any acknowledgement or other feedback from the ED 104. For example, the IMD 102 can output a notification sequence of pulses, using at least two of its therapeutic electrodes 108, within a notification transmission window following the outputting of the advertisement pulse or sequence of pulses. The notification sequence of pulses is encoded with diagnostic information associated with the IMD 102 and/or associated with the patient 101 within which the IMD 102 is implanted.

Figure 6B:
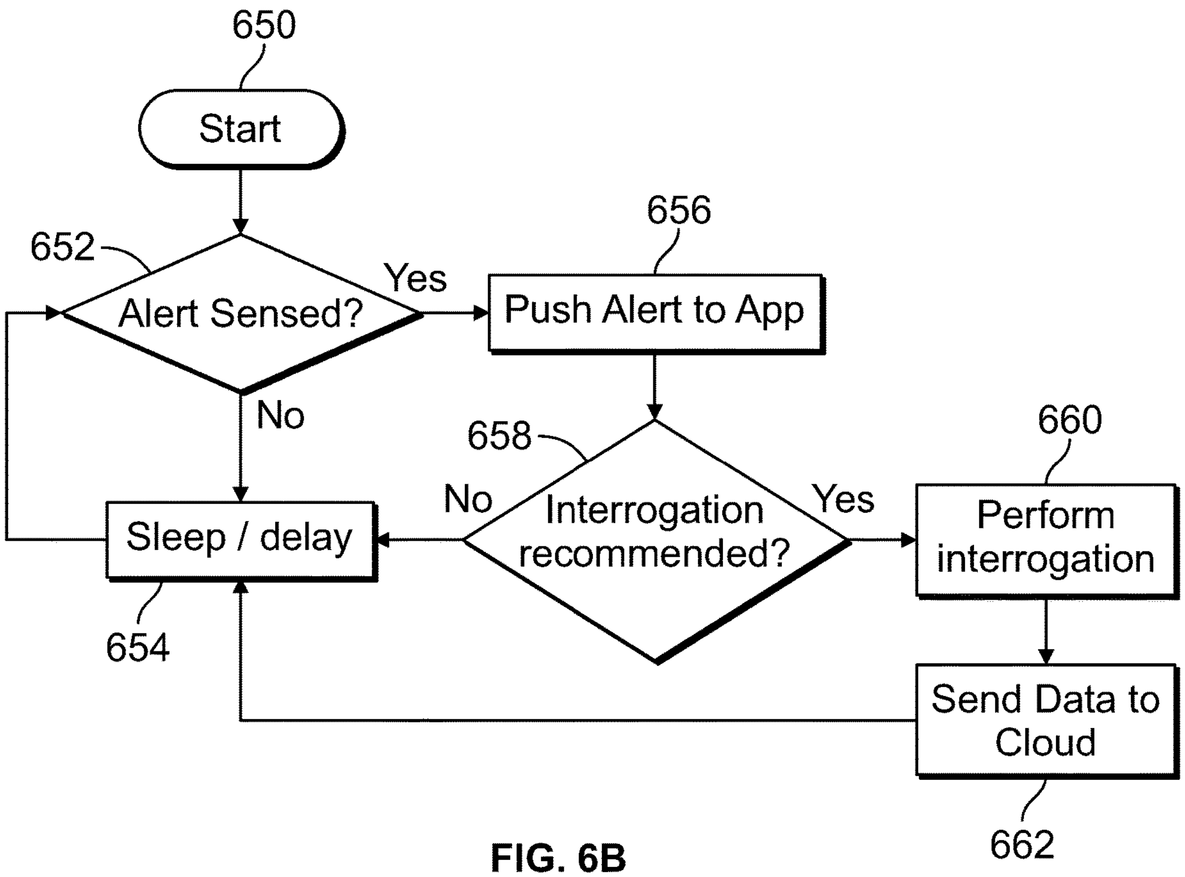
FIG. 6B shows an alert scheme that uses information transmitted between the LP and the ED to provide alerts to a patient and/or patient care network in accordance with embodiments herein.

FIG. 6B shows an alert scheme that uses information transmitted between the IMD 102 and the ED 104 as discussed in FIG. 6A to provide alerts to a patient 101 and/or patient care network in accordance with embodiments herein. The operations of FIG. 6B may be implemented by hardware, firmware, circuitry and/or one or more processors housed partially and/or entirely within an ED 104 or IMD 102, 109, a local external device, remote server or more generally within a health care system. Optionally, the operations of FIG. 6B may be partially implemented by an IMD 102, 109 and partially implemented by a local external device, remote server or more generally within a health care system. For example, the IMD 102, 109 includes IMD memory and one or more IMD processors, while each of the external devices/systems (e.g., local, remote or anywhere within the health care system) include external device memory and one or more external device processors.

At 650, one or more processors start the ED 104 and/or a timer can be set between listening events. For example, the ED 104 may be programmed to scan for conductive communication signals between a set time period, such as between 9:00 pm and 6:00 am, the ED 104 can be manually turned on, and/or the ED 104 can be remotely turned on such as from a remote server or health care system.

At 652, the one or more processors monitor the identified configuration of external electrodes 106 to sense conductive communication signals transmitted by the IMD 102. If no conductive communication signals are detected, flow passes to 654 where the one or more processors initiate a delay or sleep mode of the ED 104 before returning to 652 to monitor for signals. If the external electrodes 106 sense the conductive communication signals and the one or more processors decode the notification sequence(s), flow passes to 656.

At 656, the one or more processors can push an alert to an application ("app") that can be, for example, on a patient's or caregiver's smart phone, or housed within the ED 104 or other device. In some embodiments, the one or more processors can generate external communication(s) including phone calls, emails, text messages, cell/smart phone notifications, etc. In some cases, alerts can be in different categories or levels depending upon severity. By way of example only, an alert can indicate an abnormal condition sensed by the IMD 102, a failure or potential failure within the IMD 102, a serious or concerning condition experienced by the patient 101, and the like. Nonlimiting examples of alerts can be a low battery, a change in programming, an error detected, and the like. In other embodiments, depending upon the severity of an alert, the ED 104 can initiate an alarm and/or treatment notification, such as a noise, vibration, and the like. In some embodiments, the alerts can be categorized into device safety and performance, clinical events for patient management, optimization and/or information updates.

At 658, the one or more processors determine if an interrogation of the IMD 102 or other IMD should be conducted. If an interrogation is not recommended, flow passes to 654. If an interrogation is recommended, flow passes to 660, where the one or more processors perform an interrogation of the IMD 102. By way of example only, an interrogation level can be based on a level of the alert. For example, if a higher-level alert is received, the one or more processors may complete a more robust and/or full interrogation of the IMD 102 to gather all relevant logs and/or other data. If a low-level alert is received, the interrogation may gather the alert messages, which may be less resource intensive and require less battery power. In further embodiments, a recurring data collection interrogation can also be used that is based on the information alert with the intent of collecting continuous data for trends and the like.

At 662, the one or more processors send data transferred from the IMD 102 through the conductive communication signals sensed by the external electrodes 106 to the Cloud, a server, or other identified location for storage and/or further analysis and/or processing. In some cases, if less data was gathered at 660, such as associated with a low-level alert, less battery power is needed and the burden on the telemetry system is reduced. In some embodiments, the IMD 102 may send the data when a minimum amount of data has been collected, further saving battery power.

Remote Monitor

FIG. 7 is a block diagram illustrating an exemplary remote monitor in accordance with embodiments herein, wherein the remote monitor can also be referred to as an external remote monitor or external device (ED) 702. The term external, as used in these phrases, means the monitor/device is not implanted within a patient, and is not configured for implantation.

The ED 702 can be used to receive diagnostic information from the IMD 102 or other IMD 109 from time to time without requiring the use of an external programmer (not shown) that is used to, for example, download new operational parameters to the IMD 102. In contrast to an external programmer, the ED 702 (aka remote monitor) is incapable of programming the IMD 102 or otherwise directly altering any therapy functionality of the IMD 102 from which ED 702 obtains information. Accordingly, if the ED 702 obtains information from the IMD 102 that indicates that certain modifications should be made to the IMD 102, ED 702 can either provide a patient notification that informs the patient they should visit a medical facility, and/or the ED 702 can transmit a notification and/or other information to a patient care network. Accordingly, it should be appreciated that the ED 702 may be less sophisticated than a typical external programmer, and/or can be implemented (at least partially) using a smart phone or the like, to enable such an external device to be more affordable and more readily available to patients to provide for remote follow-up capabilities. Thus, it should be appreciated that patients that own or otherwise have access to the ED 702 may not be required to visit a medical facility as often as they would otherwise need to if they did not own or otherwise have access to the ED 702.

As will be explained in additional details below and in, for example, FIG. 6A, in some embodiments, the ED 702 can send an acknowledgement sequence of pulses, which informs an IMD 102 that the ED 702 is in proximity to the IMD 102 and capable of receiving data (encoded into conductive communication pulses) from the IMD 102.

FIG. 7 shows an embodiment of the ED 702 adapted for receiving conductive communication signals from the IMD 102, in order to perform remote monitoring of the IMD 102. The ED 702 is shown as including a controller 712, a display 716, a user interface 718, a network interface 720, and a battery/supply regulator 726. The battery and/or supply regulator 726 provides one or more constant voltages to the various components of the ED 702 during normal operation. The ED 702 is also shown as including a conductive communication receiver (RX) 742, and a conductive communication transmitter (TX) 732. The receiver 742, in this example embodiment, is shown as including a message amplifier, differential circuit and/or filter 740, and a message decoder 738, and is configured to receive conductive communication signals from the IMD 102. The controller 712, which is used to control the operation of the ED 702, can include, e.g., one or more processors (or equivalent control circuitry), RAM and/or ROM memory, logic and timing circuitry, state machine circuitry, and/or I/O circuitry, but is not limited thereto. The controller 712 can also include a clock circuit, or a separate clock circuit (not shown) can provide a clock signal to the controller 712. In some embodiments, the controller 712 can be a digital signal processor (DSP) capable of processing an incoming message that is in a biphasic waveform within a predetermined window, such as around 30 microseconds, and providing a response to be transmitted back to the IMD 102 in the next window. Accordingly, the toggling between transmit and receive occurs during the length of approximately one window. In other embodiments, the controller 712 can be a field-programmable gate array (FPGA).

The ED 702 is connected to three external electrodes 715*a*, 715*b*, and 715*c* (e.g., capacitive electrodes), which can be referred to collectively as the external electrodes 715, or individually as an external electrode 715. At least one of the external electrodes 715 is separated apart from the skin of a patient with a dielectric layer 717*a*, 717*b*, 717*c*. In the example shown, each of the three external electrodes 715 are separated apart from the skin with a corresponding dielectric layer 717. In other embodiments, an active surface of one or more of the external electrodes 715 is in contact with the patient's skin. For example, the active surface of one or two of the external electrodes 715 can be configured to be touched by one or more digits on a hand of a patient, or to come into contact with a patient's wrist, chest, leg, and the like, but are not limited thereto. In other embodiments, the ED 702 can include or be coupled to more than three external electrodes 715. In some embodiments, one or more external electrode 715 may be tied together for form a larger contact.

The external electrodes 715 can be located on a housing of the ED 702, or can be separate from such a housing. Where the external electrodes 715 are separate from a housing of the ED 702, the external electrodes 715 can be attached to a further housing that is communicatively coupled to the ED 702 via one or more wires, or via a wireless connection, e.g., using Bluetooth or WiFi, but not limited thereto. The external electrodes 715, as will be described in more detail below, can be used to receive conductive communication signals from the IMD 102.

The external electrodes 715 are connected to a multiplexor or switches 713 (e.g., switching block 506 of FIG. 5), which is shown as including first and second sets of switches 713*a*, 713*b* for connecting the identified subset/configuration of the external electrodes 715 to the receiver 742 and the transmitter 732. The various sets of switches are controlled by the controller 712 and can be based on the output voltage level 723 of the message amplifier, differential circuit and/or filter 740. In certain embodiments, the amplifier, differential circuit and/or filter 740 includes differential circuits that are connected to a pair of the external electrodes 715 by the switches 713 under the control of the controller 712. As an example, the switches 713*a* can be controlled to connect any pair of the external electrodes 715*a*, 715*b*, 715*c* as inputs (e.g., sense electrodes) to the message amplifier, differential circuit and/or filter 740. The same pair of the external electrodes 715 are connected as outputs of the transmitter 732. The third electrode 715, in this example, is connected to a ground connection of the receiver 742 and optionally the transmitter 732. For example, the switches 713*a* can connect the external electrode 715*a* to a first input 719*a* of the message amplifier, differential circuit and/or filter 740, the external electrode 715*b* to a second input 719*b* of the message amplifier, differential circuit and/or filter 740, and the external electrode 715*c* to active ground/passive ground 721. The feedback signal 524 (of FIG. 5), provided via the ground connection is fed back into the patient through the ground 721 to at least partially remove a common mode component within the conductive communication signals. The use of the multiplexor enables selection from among the multiple sensing vectors for conductive communication with the implanted IMD 102, as discussed previously, so that system signal-to-noise ratio can be improved or maximized.

As noted above, the conductive communication receiver 742, which is shown as including the message amplifier, differential circuit and/or filter 740, and the message decoder 738, is configured to receive conductive communication signals from the IMD 102. The message amplifier, differential circuit and/or filter 740 is configured to amplify, process, and/or filter conductive communication signals received from the IMD 102. The amplifier portion can be used to increase the relatively small amplitudes of such conductive communication signals. The differential circuit portion outputs a difference between input signals, and the filter portion can be a high-pass filter or a bandpass filter, for example. The message decoder 738 can be configured to decode conductive communication signals received from an IMD 102 into a format that the controller 712 can understand. For example, the message decoder 738 can process the output of the message amplifier, differential circuit and/or filter 740 to identify a communications message transmitted from the ED 104 within the conductive communication signals. The specific type of decoding performed by the message decoder 738 depends upon the specific coding of the conductive communication signals received from an IMD 102, e.g., on-off keying, frequency-shift keying, frequency modulation, or amplitude shift keying, but not limited thereto.

The conductive communication transmitter 732 is configured to send (under the control of the controller 712) a remote monitor acknowledgement (ACK) sequence of conductive communication pulses, which informs the IMD 102 that the ED 702 is in proximity to the IMD 102 and capable of receiving data (encoded into conducted communicate pulses) from the IMD 102 as discussed in FIG. 6A.

The transmitter 732, in this example embodiment, is shown as including a message encoder and/or modulator 730 and an amplifier 736. The message encoder and/or modulator 730 can be configured to encode and/or modulate signals that are output from the controller 712 into a format that IMD 102 can understand. The specific type of encoding performed by the message encoder depends upon the specific type of encoding the IMD 102 can understand, e.g., on-off keying, frequency-shift keying, frequency modulation, or amplitude shift keying, but not limited thereto. The amplifier 736 is coupled to the encoder/modulator 730 to increase amplitudes of pulses included in an ACK sequence to a level sufficient to enable an IMD 102 to receive acknowledgements from the ED 702.

The controller 712 receives data and optionally displays, using the display 716, information included in data acquired from the implanted IMD 102 acquired through the encoded pulses included in conductive communication signals, such as battery voltage, lead impedance, sensed cardiac signal amplitude, or other system status information. The controller 712 also can accept input from a user via a user interface 718, which can include, e.g., a keyboard and/or touch-screen, but is not limited thereto. The controller 712 can also communicate over a network interface 720 to other data entry or display units, such as a handheld computer or laptop/desktop unit. The network interface 720 can be cabled or wireless and can also enable communication to a local area network or the Internet for greater connectivity. More specifically, the network interface 720 can be used to send diagnostic data and other types of data collected from the IMD 102 to a patient care network associated with a medical group and/or facility. For more specific examples, the network interface can include a Bluetooth antenna, a Wi-Fi antenna, and/or an Ethernet connection, but is not limited thereto.

The controller 712, which can include one or more processors, and/or the like, can execute operations based on firmware stored in non-volatile memory (Flash). The non-volatile memory can also be used to store parameters or values that are to be maintained when power is removed. The controller 712 can use volatile memory or random access memory (RAM) as general storage for information such as ECG data, status information, swap memory, and other data.

The ED 702 can take many physical forms, but fundamentally it should be able to establish a conductive vector with the patient so that it can detect the LP's conductively communicated transmissions, decipher the communication protocol utilized by the IMD 102, and upload any acquired follow-up information to a patient care network, such as the Merlin.net™ patient care network operated by Abbott Laboratories (headquartered in the Abbott Park Business Center in Lake Bluff, Ill.). In certain embodiments that utilize a specific remote follow-up protocol, the external device should also be able to transmit an appropriate code (e.g., an ACK code) to the IMD 102 per an established protocol. In this latter case, to maintain strong cybersecurity, the external device 702 may be designed such that its hardware is capable of generating and transmitting only that singular 'appropriate code' (e.g., not software-configurable).

Exemplary Form Factors

Figure 8:
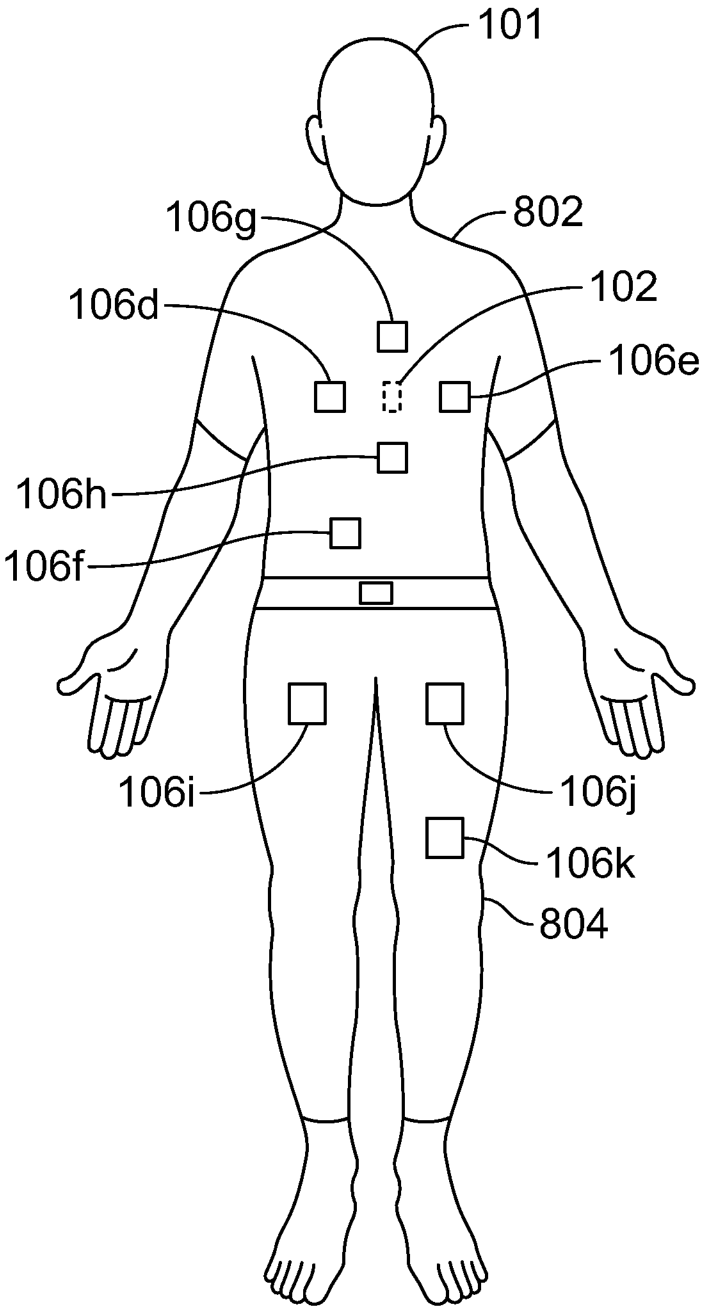
FIG. 8 shows an example of garments that hold a plurality of the external electrodes proximate to a patient's skin in accordance with embodiments herein.

FIG. 8 shows an example of garments that hold a plurality of the external electrodes **106*d*-106*k* proximate to a patient's skin in accordance with embodiments herein. Although not shown, the ED 104** can be included within the garment or other form factor to provide a self-contained device.

In the example shown, one of the garments is a shirt 802 that is sized to fit closely to the patient 101 such that the fabric of the garment is in contact with the skin. The external electrodes 106 can be positioned in various locations on/within the shirt 802, such as on the front or back side of the patient's torso, the sleeves, etc. The fabric can be any known material and may include a stretch component to ensure a snug fit to a patient's body. A dielectric layer, which can be the fabric of the shirt, spaces the active surface of at least one of the external electrodes 106 apart from the patient's skin to form the non-contact capacitively coupled interface between the patient's skin and the corresponding external electrode 106. In some embodiments, the dielectric layer spaces two, three, or more of the external electrodes 106 apart from the patient's skin, each forming a non-contact capacitively coupled interface. In some cases, the dielectric layer can be the same material as the garment. The garments and other form factors discussed herein are easy for the patient to position and use as part of daily living.

The external electrodes 106 can be the same in size as one another or different. In some embodiments the active surface area of the external electrodes 106 can be square and are approximately two inches per side and up to approximately four inches per side. In other embodiments the external electrodes 106 can be other shapes such as rectangular, circular, etc.

In this example, the IMD 102 is implanted approximately vertically within the patient 101. External electrodes **106*d*, 106*e* are positioned proximate either side of the patient's chest and on opposite sides of the IMD 102 and external electrodes 106*g*, 106*h* are positioned proximate opposite ends of the IMD 102. In some embodiments, if the IMD 102 operates as a dipole, the comparison of the external electrodes 106*d*, 106*e* (e.g., the sensing vector) positioned on either side of the IMD 102 can result in an insufficient signal differential. Therefore, after evaluating at least a portion of the sensing vectors and determining the differential signal between various sets of the external electrodes 106, the system may designate, by way of example only, external electrode 106*d* and external electrode 106*f* (positioned below the IMD 102 lower on the patient's torso) as the sensing electrodes and external electrode 106*e* as the ground electrode. In another example, the system may designate external electrodes 106*g* and 106*h* as the sensing electrodes and 106*f*** as the ground electrode.

Another of the garments shown is a pair of pants 804. The external electrodes **106*i*-106*k* can be, for example, positioned on the front thigh areas of the patient 101**, but they are not so limited.

In some embodiments, the patient 101 can use multiple separate garments at a time, such that the external electrodes 106 within multiple garments (e.g., the shirt 802 and the pants 804) are configured to be in conductive communication with the ED 104. The ED 104 can thus select the configuration of external electrodes 106 that provides the greatest signal level, as discussed previously, if more than three external electrodes 106 are available.

Each external electrode 106 is positioned such that it does not touch any other external electrode 106. In some embodiments the external electrodes 106 are also positioned such that each has the greatest likelihood of remaining coupled to the patient 101. For example, physical size of the patient 101 may be taken into consideration. In some embodiments, if a patient 101 is thin, it may be more desirable to locate the external electrodes 106 proximate the torso and/or thigh rather than the sleeve.

In other embodiments, the patient 101 can hold a separate external electrode 106 (not shown), such as to the outer surface of their pants on their thigh so that the external electrode 106 forms a non-contact capacitively coupled interface between the patient's skin and the external electrode 106 while the ED 104 connects with and receives data from the IMD 102. In some cases, one or more external electrodes 106 can be provided on an outer surface of the ED 104, allowing the user to place one or more fingers on each provided external electrode 106.

In still further embodiments, the external electrodes 106 can be provided within bedding, such as a pillow and/or blanket. The external electrodes 106 can be included in the pillow, such as to be under the patient's shoulders, upper back, and/or mid-back, to form the non-contact capacitively coupled interface. A plurality of the external electrodes 106 can be positioned within the blanket that is configured to be placed over the prone patient 101. Some form factors such as pillows and blankets are larger in size and can include an increased number of external electrodes 106 to improve reliability, while ensuring that the external electrodes 106 are spaced apart from each other so that they do not touch and create a shorted circuit. In this example, the blanket may also include the ED 104, and in some cases may be provided with an external cord and power plug similar to an electric blanket. The blanket may also be weighted to increase the contact between the dielectric layer and the patient 101.

Accordingly, the external electrodes 106 can be integrated into a variety of different form factors that can be utilized alone or together. Further, a technical advantage of at least some embodiments is the ability of the ED 104 to achieve passive remote monitoring by gathering information collected by the IMD 102 without requiring the active participation of the patient 101. Also, another advantage is the ability of the ED 104 to gather information and/or monitor for alerts over an extended period of time, such as when a patient 101 is sleeping. The form factors allow the patient 101 to move while data is collected, both while sleeping and while accomplishing normal daily tasks, for example. These advantages among others can increase a patient's compliance with using the system 100 which can improve the level of health care provided to the patient 101 as well as decrease costs.

In accordance with new and unique aspects, the system 100 delivers the particular treatment and prophylaxis for the medical conditions addressed with LPs and other cardiac IMDs, such as arrhythmia (e.g., MVT, SVT, PVT, etc.), a non-cardiac physiological condition detection, an increased pacing burden detection, an automatic mode switching (AMS) detection, a pacemaker mediated tachycardia (PMT) detection, a premature ventricular contraction (PVC) detection, and/or the like. The ED 104 can gather information at any time through conductive communication with the IMD 102, 109 without the patient 101 needing to come to a facility, such as at predetermined times, on-demand by the patient 101, or remotely requested over the patient care network. For example, cardiac activity data collected by the IMD 102 can be used to confirm that an arrhythmia exists and to determine whether the arrhythmia requires treatment. Further, alerts can be generated to inform the patient 101 and/or practitioner that a condition has been detected, and in some cases can suggest an action such as requesting emergency assistance, scheduling an exam, etc. Also, the level of treatment to be administered to the patient 101 can be determined, such as no treatment, delay in treatment, pacing therapy, high-level shock treatment (e.g., shock therapy delivery), need to schedule battery replacement, adjustment of thresholds, etc.

Remote External Device

Figure 9:
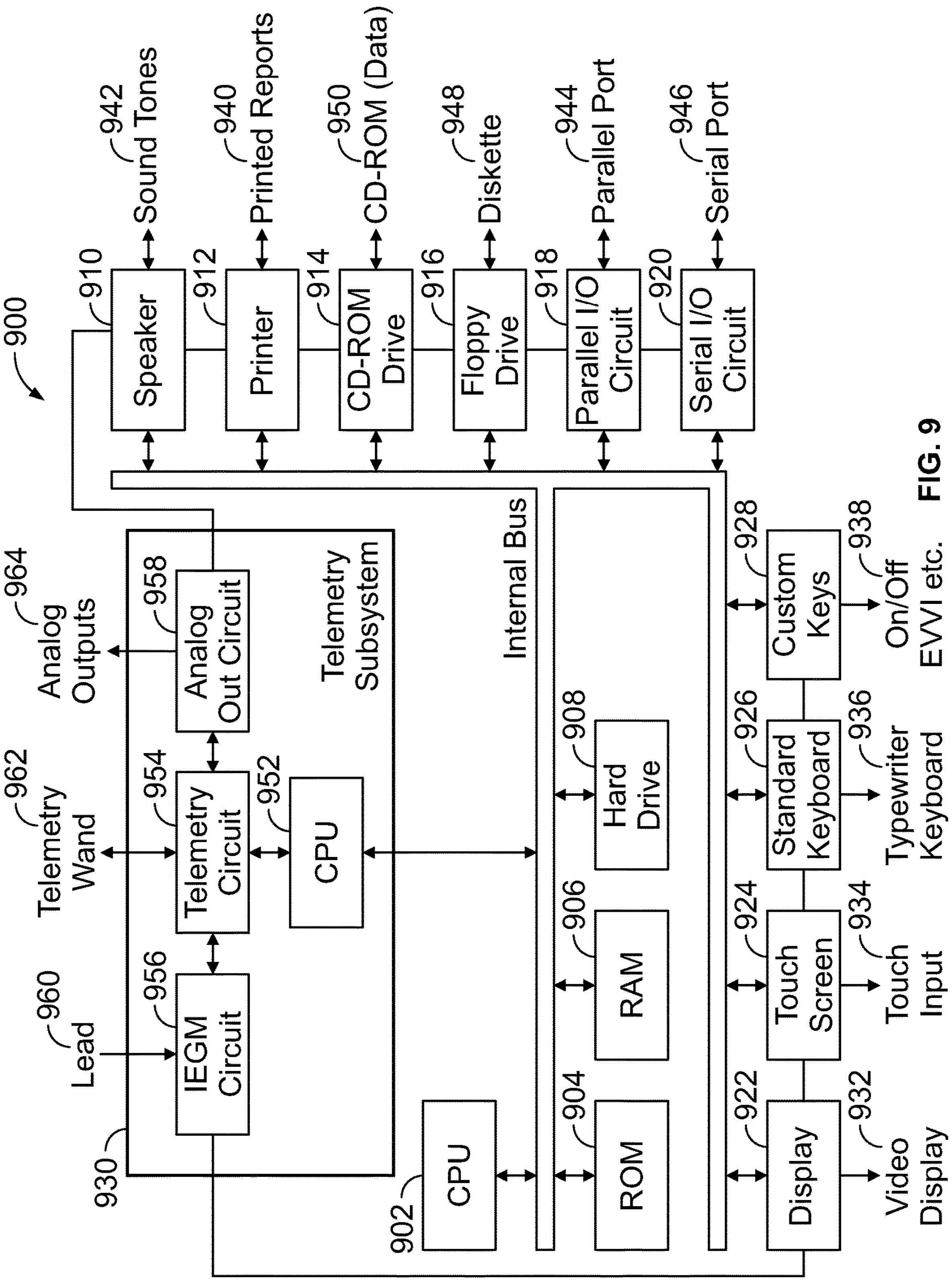
FIG. 9 illustrates a functional block diagram of the external device that is operated in accordance with embodiments herein.

FIG. 9 illustrates a functional block diagram of the external device (ED) 900 that is operated in accordance with the processes described herein and to interface with implantable medical devices such as the IMD 102 as described herein. The external device 900 may be a workstation, a portable computer, a PDA, a cell phone and the like. The external device 900 includes an internal bus that connects/interfaces with a Central Processing Unit (CPU) 902, ROM 904, RAM 906, a hard drive 908, the speaker 910, a printer 912, a CD-ROM drive 914, a floppy drive 916, a parallel I/O circuit 918, a serial I/O circuit 920, the display 922, a touch screen 924, a standard keyboard connection 926, custom keys 928, and a telemetry subsystem 930. The internal bus is an address/data bus that transfers information between the various components described herein. The hard drive 908 may store operational programs as well as data, such as waveform templates and detection thresholds.

The CPU 902 typically includes a microprocessor, a micro-controller, or equivalent control circuitry, designed specifically to control interfacing with the external device 900 and with the external electrodes 106. The CPU 902 performs the processes discussed herein. For example, the CPU 902 may perform all or a portion of the determinations of the sensing vectors, identification of the configurations of the external electrodes 106 with respect to sensing electrodes and ground electrode, determining whether the ED 104 should be interrogated, initiating alerts, and the like.

The CPU 902 may include RAM or ROM memory, logic and timing circuitry, state machine circuitry, differential amplification and processing circuitry, and I/O circuitry to interface with the IMD 102 and external electrodes 106. The display 922 (e.g., may be connected to the video display 932). The touch screen 924 may display graphic information relating to the IMD 102. The display 922 displays various information related to the processes described herein. The touch screen 924 accepts a user's touch input 934 when selections are made. The keyboard 926 (e.g., a typewriter keyboard 936) allows the user to enter data to the displayed fields, as well as interface with the telemetry subsystem 930. Furthermore, custom keys 928 turn on/off 938 (e.g., EVVI) the external device 900. The printer 912 prints copies of reports 940 for a physician to review or to be placed in a patient file, and speaker 910 provides an audible warning (e.g., sounds and tones 942) to the user. The parallel I/O circuit 918 interfaces with a parallel port 944. The serial I/O circuit 920 interfaces with a serial port 946. The floppy drive 916 accepts diskettes 948. Optionally, the floppy drive 916 may include a USB port or other interface capable of communicating with a USB device such as a memory stick. The CD-ROM drive 914 accepts CD ROMs 950.

The telemetry subsystem 930 includes a central processing unit (CPU) 952 in electrical communication with a telemetry circuit 954, which communicates with both an intracardiac electrogram (IEGM) circuit 956 and an analog out circuit 958. Optionally, the circuit 956 may be connected to leads 960.

The telemetry circuit 954 is connected to a telemetry wand 962. The analog out circuit 958 includes communication circuits to communicate with analog outputs 964. The external device 900 may wirelessly communicate with the IMD and utilize protocols, such as Bluetooth, GSM, infrared wireless LANs, HIPERLAN, 3G, satellite, as well as circuit and packet data protocols, and the like. Alternatively, a hard-wired connection may be used to connect the external device 900 to the IMD.

Alternative Device Implementations

While the foregoing embodiments are described primarily in connection with leadless pacemakers, it is understood that embodiments may be implemented in connection with one or more other types of implantable medical devices (IMDs). Non-limiting examples of IMDs include one or more of neurostimulator devices, implantable leadless monitoring devices, body generated analyte (BGA) test devices and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 entitled "Neurostimulation Method And System To Treat Apnea", U.S. Pat. No. 9,044,610 entitled "System And Methods For Providing A Distributed Virtual Stimulation Cathode For Use With An Implantable Neurostimulation System", U.S. Pat. No. 10,549,105 entitled "Apparatuses and methods that improve conductive communication between external programmers and implantable medical devices", U.S. Patent Publication 20210308470A1 entitled "Remote follow-up methods, systems, and devices for leadless pacemaker systems", published Oct. 7, 2021, and U.S. Pat. No. 9,522,280 entitled "Leadless dual-chamber pacing system and method", which are hereby incorporated by reference.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, the IMD may be a subcutaneous IMD that includes one or more structural and/or functional aspects of the device(s) described in U.S. Pat. No. 10,765,860, titled "Subcutaneous Implantation Medical Device With Multiple Parasternal-Anterior Electrodes"; U.S. Pat. No. 10,722,704, titled "Implantable Medical Systems And Methods Including Pulse Generators And Leads"; U.S. Pat. No. 11,045,643, titled "Single Site Implantation Methods For Medical Devices Having Multiple Leads", which are hereby incorporated by reference in their entireties. Further, one or more combinations of IMDs may be utilized from the above incorporated patents and applications in accordance with embodiments herein. Additionally or alternatively, the IMD may be a leadless cardiac monitor (ICM) that includes one or more structural and/or functional aspects of the device(s) described in U.S. Pat. No. 9,949,660, entitled, "METHOD AND SYSTEM TO DISCRIMINATE RHYTHM PATTERNS IN CARDIAC ACTIVITY," which is expressly incorporated herein by reference. Embodiments may be implemented utilizing all or portions of the methods and systems described in U.S. application Ser. No. 16/930,791, filed Jul. 16, 2020 and titled "METHODS, DEVICES AND SYSTEMS FOR HOLISTIC INTEGRATED HEALTHCARE PATIENT MANAGEMENT", (Publication No. 2021/0020294), publishing Jan. 21, 2021, which is expressly incorporated herein by reference.

Additionally or alternatively, the IMD and ED may include one or more structural and/or functional aspects of the device(s) described in U.S. Pat. No. 11,357,414, entitled "Methods, systems and devices that use conductive communication to determine time delay for use in monitoring blood pressure", which is expressly incorporated herein by reference. Embodiments may be implemented utilizing all or portions of the methods and systems described in U.S. application Ser. No. 17/222,242, filed Apr. 5, 2021 and titled "REMOTE FOLLOW-UP METHODS, SYSTEMS, AND DEVICES FOR LEADLESS PACEMAKER SYSTEMS", (Publication No. 2021/0308470), publishing Oct. 7, 2021, which is expressly incorporated herein by reference.

Additionally or alternatively, the IMD may be a "BGA test device" utilized to collect and analyze a body generated analyte (BGA). The BGA test device may implement one or more of the methods, devices and systems described in the following publications, all of which are incorporated herein by reference in their entireties: U.S. Patent Publication Number 2011/0256024, entitled "MODULAR ANALYTE MONITORING DEVICE", published Oct. 20, 2011; U.S. Patent Publication Number 2010/0198142, entitled "MULTIFUNCTION ANALYTE TEST DEVICE AND METHODS THEREFORE", published Aug. 5, 2010; U.S. Patent Publication Number 2011/0160544, entitled "SYSTEM AND METHOD FOR ANALYSIS OF MEDICAL DATA TO ENCOURAGE HEALTHCARE MANAGEMENT", published Jun. 30, 2011; U.S. Pat. No. 5,294,404, entitled "REAGENT PACK FOR IMMUNOASSAYS" issued Mar. 15, 1994; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publication Number 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23, 2010; U.S. Pat. No. 7,723,099, entitled "IMMUNOASSAY DEVICE WITH IMMUNO-REFERENCE ELECTRODE" issued May 25, 2010; and Baj-Rossi et al. "FABRICATION AND PACKAGING OF A FULLY IMPLANTABLE BIOSENSOR ARRAY", (2013) IEEE, pages 166-169.

All references, including publications, patent applications and patents, cited herein are hereby incorporated by reference to the same extent as if each reference were individually and specifically indicated to be incorporated by reference and were set forth in its entirety herein.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Some or all of the Figures herein illustrate various methods and processes implemented in accordance with embodiments herein. The operations herein may be implemented by hardware, firmware, circuitry and/or one or more processors housed partially an/or entirely within an IMD, a local external device, remote server or more generally within a health care system. Optionally, the operations herein may be partially implemented by an IMD and partially implemented by a local external device, remote server or more generally within a health care system. For example, the IMD includes IMD memory and one or more IMD processors, while each of the external devices/systems (ED) (e.g., local, remote or anywhere within the health care system) include ED memory and one or more ED processors.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage media having computer (device) readable program code embodied thereon.

Any combination of at least one non-signal computer (device) readable medium may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It should be recognized that, to the extent embodiments herein are described to apply certain mathematical combinations of select variables, the same variables may be combined in other mathematical combinations that are also indicative of the same result. For example, when a single data point is utilized for a particular variable, additionally or alternatively, a mean, average, sum, or other mathematical combination of multiple data points may be utilized for the same variable.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A device, comprising:

external electrodes configured to be held proximate to a skin of a patient and to sense conductive communication signals transmitted by an implantable medical device (IMD) within the patient through therapeutic electrodes of the IMD that are also configured for at least one of pacing or sensing;

a dielectric layer provided on at least a first electrode from the external electrodes to space the first electrode apart from the skin of the patient to form a non-contact capacitively coupled interface between the skin of the patient and the first electrode, the capacitively coupled interface sensitive to the conductive communication signals;

a circuit connected to the external electrodes, the circuit configured to output a differential signal corresponding to the conductive communication signals;

a switching block configured to selectively connect different pairs of the external electrodes as sense electrodes and to selectively connect another external electrode from the external electrodes as a ground electrode; and one or more processors configured to control the switching block to monitor for the conductive communication signals using a plurality of sensing vectors corresponding to the different pairs of the external electrodes, determine a differential signal associated with each of the sensing vectors, and select, as an active sensing configuration for sensing the conductive communication signals, one of the different pairs of the external electrodes based on a comparison of the differential signals that are determined.

2. The device of claim 1, wherein the external electrodes comprise the first electrode, a second electrode, and the ground electrode, the first and second electrodes configured to sense the conductive communication signals, the ground electrode configured to form at least one of a passive or driven grounding node to the skin.

3. The device of claim 2, wherein at least two of the first electrode, the second electrode, and the ground electrode are spaced apart from the skin by an additional dielectric layer.

4. The device of claim 2, wherein the circuit further comprises a feedback circuit joined to the ground electrode to form the driven grounding node, the feedback circuit configured to supply a feedback signal back into the patient to at least partially remove a common mode component within the conductive communication signals sensed by the first and second electrodes.

5. The device of claim 2, wherein the non-contact capacitively coupled interface includes a thin layer of an insulating material, as the dielectric layer, to separate metal surfaces of the first and second electrodes from the skin of the patient, the non-contact capacitively coupled interface configured to pass the conductive communication signals with a frequency of at least 100 KHz and to block or at least partially attenuate signals below 100 kHz.

6. The device of claim 1, wherein the circuit includes a differential circuit configured to detect a potential difference, exhibited between the first electrode and a second electrode from the external electrodes, due to the conductive communication signals.

7. The device of claim 6, wherein the first and second electrodes are configured to receive the conductive communication signals having a frequency of at least 100 KHz.

8. The device of claim 1, wherein the one or more processors are configured to process the differential signal to identify a communications message transmitted from the IMD within the conductive communication signals.

9. The device of claim 8, wherein the one or more processors are configured to process the differential signal by detecting a pulse train including the communications message.

10. The device of claim 9, wherein the one or more processors are configured to process the differential signal by detecting a first pulse having a first frequency followed by the pulse train having a second frequency.

11. The device of claim 1, further comprising a garment configured to hold the external electrodes proximate to the skin of the patient, the garment including the dielectric layer to space the first electrode apart from the skin of the patient to form the non-contact capacitively coupled interface between the skin of the patient and the first electrode.

12. An external device, comprising:

a plurality of external electrodes configured to be held proximate to a skin of a patient and to sense conductive communication signals transmitted by an implantable medical device (IMD) within the patient through therapeutic electrodes of the IMD that are also configured for at least one of pacing or sensing;

a dielectric layer provided on at least a first external electrode from the plurality of external electrodes to space the first external electrode apart from the skin of the patient to form a non-contact capacitively coupled interface between the skin of the patient and the first external electrode, the non-contact capacitively coupled interface sensitive to the conductive communication signals;

a circuit connected to the plurality of external electrodes, the circuit configured to output a differential signal corresponding to the conductive communication signals;

a switching block configured to selectively connect different pairs of the plurality of external electrodes to the circuit as sense electrodes and to selectively connect, as a ground electrode, an external electrode of the plurality of external electrodes that is not included in a selected pair of the different pairs; and one or more processors configured to control the switching block to monitor for the conductive communication signals using a plurality of sensing vectors corresponding to the different pairs of the plurality of external electrodes, determine a differential signal associated with each of the plurality of sensing vectors, and select, as an active sensing configuration for sensing the conductive communication signals, one of the different pairs of the plurality of external electrodes based on the differential signals.

13. The external device of claim 12, wherein the one or more processors are configured to select the one of the different pairs of the plurality of external electrodes based on the sensing vector having a largest differential signal.

14. The external device of claim 12, wherein the ground electrode is configured to form at least one of a passive or driven grounding node to the skin.

15. The external device of claim 14, wherein the circuit further comprises a feedback circuit joined to the ground electrode to form the driven grounding node, the feedback circuit configured to supply a feedback signal back into the patient through the ground electrode to at least partially remove a common mode component within the conductive communication signals sensed by the active sensing configuration.

16. The external device of claim 12, wherein at least one external electrode of the selected pair or the ground electrode is spaced apart from the skin of the patient by an additional dielectric layer.

17. An external device configured to sense conductive communication signals transmitted by an implantable medical device (IMD) implanted within a patient and having therapeutic electrodes for at least one of pacing or sensing and for transmitting conductive communication signals through tissue of the patient, the external device comprising:

external electrodes configured to be held proximate to skin of the patient;

a dielectric layer provided on at least a first external electrode from the external electrodes to space the first external electrode apart from the skin of the patient to form a non-contact capacitively coupled interface between the skin of the patient and the first external electrode, the non-contact capacitively coupled interface sensitive to the conductive communication signals;

a differential circuit configured to output a differential signal corresponding to a potential difference, exhibited between a selected pair of the external electrodes, due to the conductive communication signals;

a switching block configured to selectively connect different pairs of the external electrodes to the differential circuit as sense electrodes and to selectively connect another external electrode from the external electrodes as a ground electrode; and a controller configured to control the switching block to test a plurality of sensing vectors corresponding to the different pairs of the external electrodes and to select one of the different pairs of the external electrodes as an active sensing configuration based on the differential signals associated with the plurality of sensing vectors.

18. The external device of claim 17, wherein the external device further comprises a garment configured to hold the external electrodes proximate to the skin of the patient.

19. The external device of claim 17, wherein the controller is configured to process the differential signal from the active sensing configuration to identify a communications message transmitted from the IMD within the conductive communication signals.

20. The external device of claim 19, wherein the controller is configured to identify the communications message by detecting a pulse train within the differential signal.

* * * * *